ized in the United States Patent and Trademark Office">

US011306121B2

(12) United States Patent
Chung et al.

(10) Patent No.: US 11,306,121 B2
(45) Date of Patent: Apr. 19, 2022

(54) COMPOSITION FOR MUSCLE RELAXATION

(71) Applicant: CAREGEN CO., LTD., Anyang-si (KR)

(72) Inventors: Yong Ji Chung, Seoul (KR); Eun Mi Kim, Yongin-si (KR); Eung Ji Lee, Anyang-si (KR)

(73) Assignee: Caregen Co., Ltd., Anyang-Si (KR)

( * ) Notice: Subject to any disclaimer, the term of this patent is extended or adjusted under 35 U.S.C. 154(b) by 0 days.

(21) Appl. No.: 17/251,609

(22) PCT Filed: Oct. 22, 2019

(86) PCT No.: PCT/KR2019/013916
§ 371 (c)(1),
(2) Date: Dec. 11, 2020

(87) PCT Pub. No.: WO2020/138674
PCT Pub. Date: Jul. 2, 2020

(65) Prior Publication Data
US 2021/0246165 A1 Aug. 12, 2021

(30) Foreign Application Priority Data

Dec. 26, 2018 (KR) .................. 10-2018-0169495
Jul. 10, 2019 (KR) .................. 10-2019-0083008

(51) Int. Cl.
*A61K 38/00* (2006.01)
*C07K 7/06* (2006.01)
*A61P 21/02* (2006.01)
*A61K 8/64* (2006.01)
*A61Q 19/08* (2006.01)

(52) U.S. Cl.
CPC .................. *C07K 7/06* (2013.01); *A61K 8/64* (2013.01); *A61P 21/02* (2018.01); *A61Q 19/08* (2013.01)

(58) Field of Classification Search
CPC ........... A61K 8/64; A61K 38/08; A61P 21/02; A61Q 19/08; A61Q 17/00; A61Q 19/008; C07K 7/06
See application file for complete search history.

(56) References Cited

U.S. PATENT DOCUMENTS 9,079,947 B2     7/2015   Marrotta
2006/0276392 A1  12/2006  Mira et al.
2009/0010965 A1  1/2009   Eisele et al.
2009/0028906 A1  1/2009   Grein et al.
2011/0027269 A1  2/2011   Marrotta et al.
2011/0052573 A1  3/2011   Marrotta
2011/0091530 A1* 4/2011   Hantash .................. A61P 17/00
                                                      424/450
2016/0039918 A1  2/2016   Marotta
2016/0185842 A1  6/2016   Marotta et al.
2016/0279193 A1  9/2016   Otterlei
2016/0289272 A1  10/2016  Otterlei et al.
2020/0157195 A1  5/2020   Marotta et al.

FOREIGN PATENT DOCUMENTS

KR    10-2010-0020972 A       2/2010
KR    10-2017-0116184 A      10/2017
KR       20170116184 A  *   10/2017   .............. A61P 37/06

OTHER PUBLICATIONS

English language translation of KR20170116184 by ESPACENET (Year: 2017).*
International Search Report and Written Opinion of the International Searching Authority for International Patent Application No. PCT/KR2019/013916 dated Jan. 29, 2020, 12 pages.
NCBI, GenBank Accession No. AMF63903.1, "Sequence 30 from U.S. Pat. No. 9,079,947", 2 pages (Feb. 10, 2016).
Broide, R. et al., "The rat Digit Abduction Score (DAS) assay: A physiological model for assessing botulinum neurotoxin-induced skeletal muscle paralysis", Toxicon, 71: 18-24 (2013).
Extended European Search Report for European Patent Application No. 19904095.7 dated Jul. 2, 2021, 9 pages.
Dressler, Dirk, "Clinical applications of boulinum toxin", Current Opinion in Microbiology, Jul. 5, 2012, pp. 325-336, vol. 15, No. 3.
Grandos, S. A. et al., "The non-neuronal and nonmuscular effects of botulinum toxin: an opportunity for a deadly molecule to treat disease in the skin and beyond", British Journal of Dermatology, May 1, 2018, pp. 1011-1019, vol. 178, No. 5.

* cited by examiner

*Primary Examiner* — Aradhana Sasan
*Assistant Examiner* — Mercy H Sabila
(74) *Attorney, Agent, or Firm* — Merchant & Gould P.C.

(57) ABSTRACT

The present invention relates to a peptide exhibiting physiological activities and a composition including the peptide. Because the peptide of the present invention exhibits various physiological activities such as muscle relaxation, skin wrinkle improvement, sebum production suppression, and the like, the peptide may be used as an active ingredient in a pharmaceutical composition for muscle relaxation, or cosmetics for improving skin wrinkles, suppressing sebum production, or ameliorating acne.

11 Claims, 19 Drawing Sheets

Specification includes a Sequence Listing.

[Figure 1]
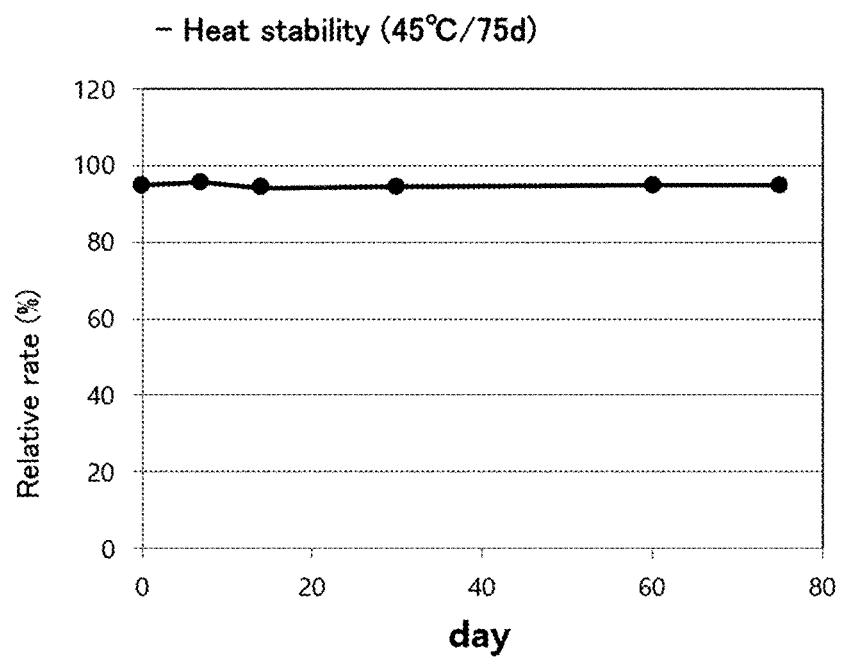

【Figure 2】
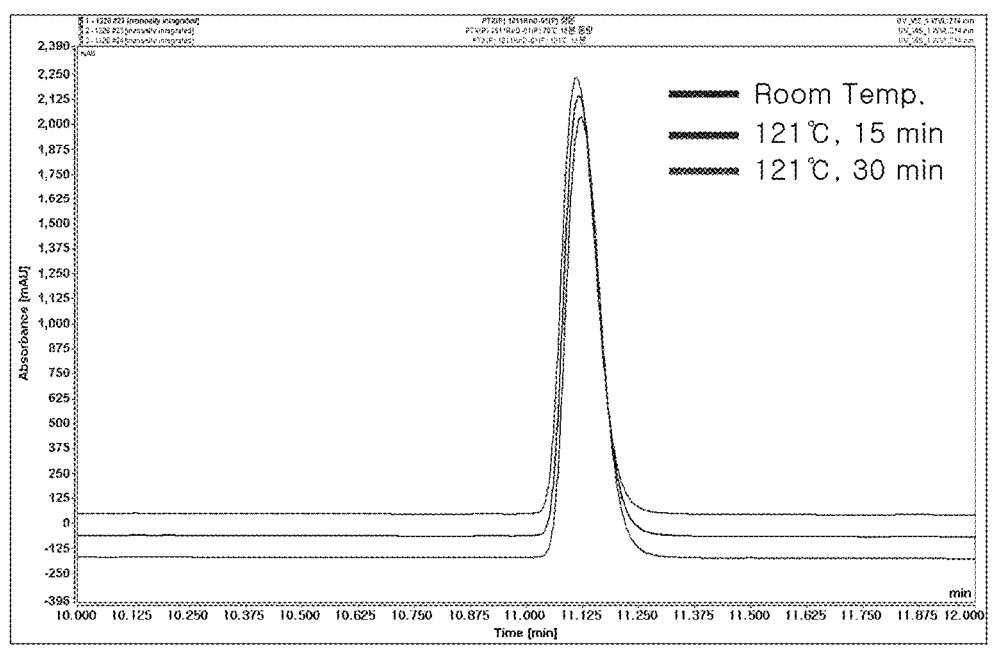

[Figure 3]
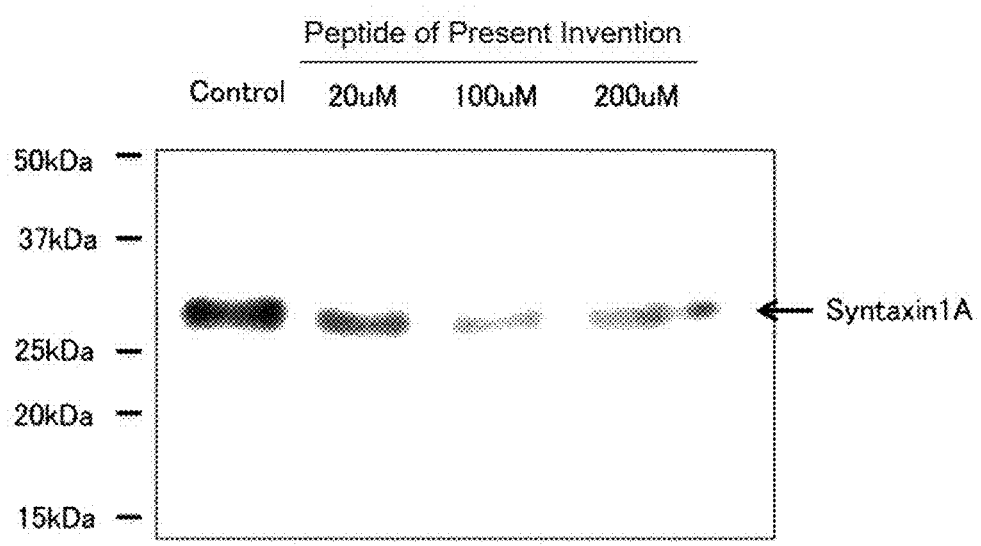
[Figure 4]
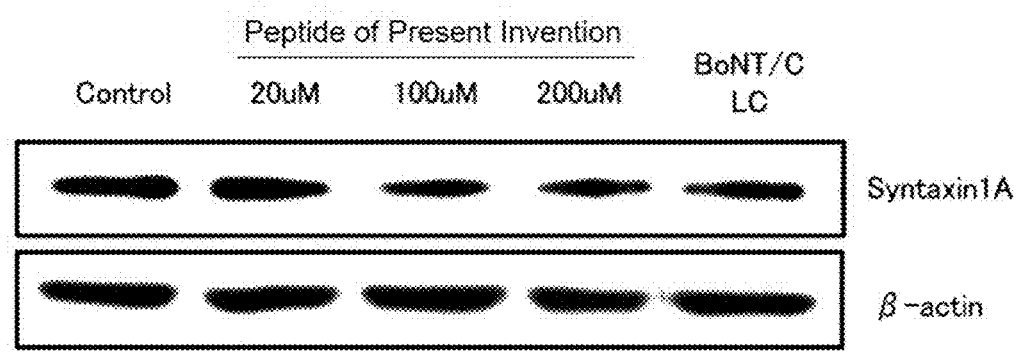

[Figure 5]
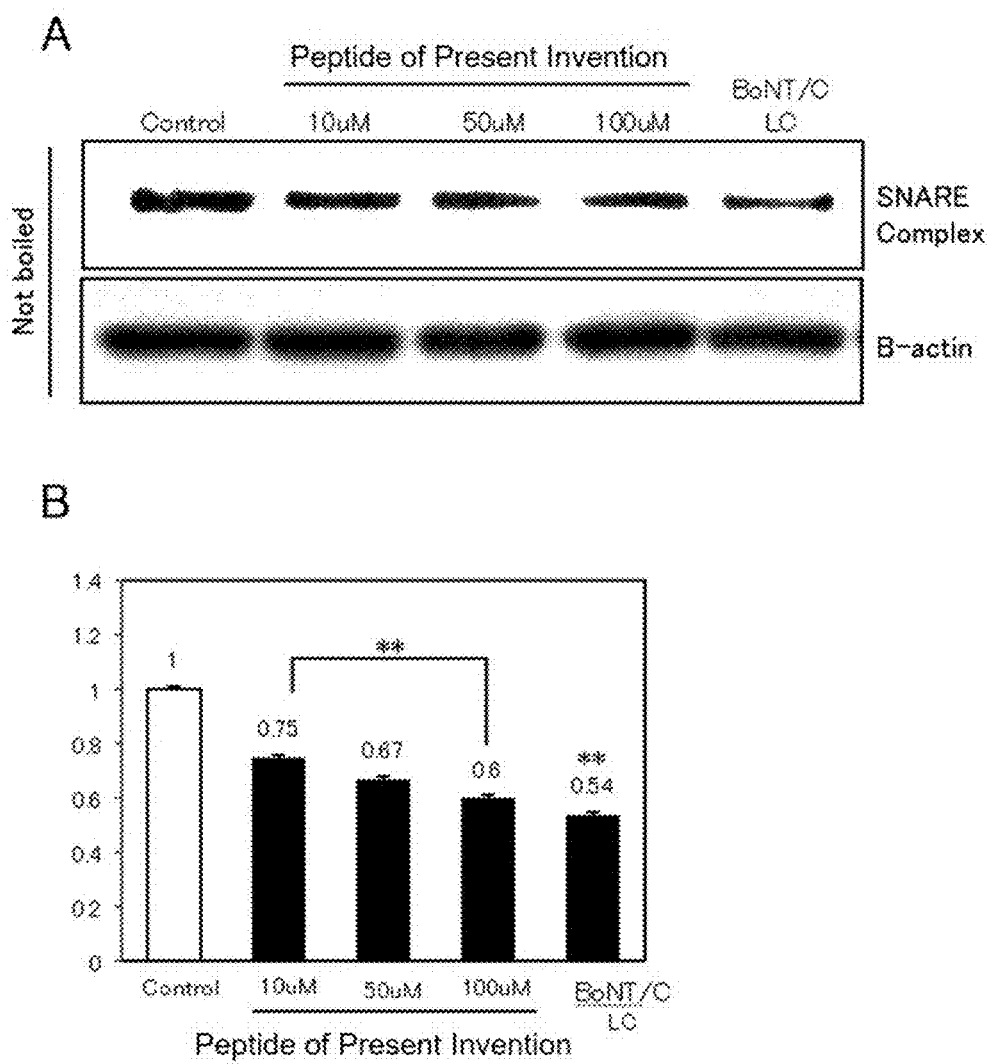

[Figure 6]
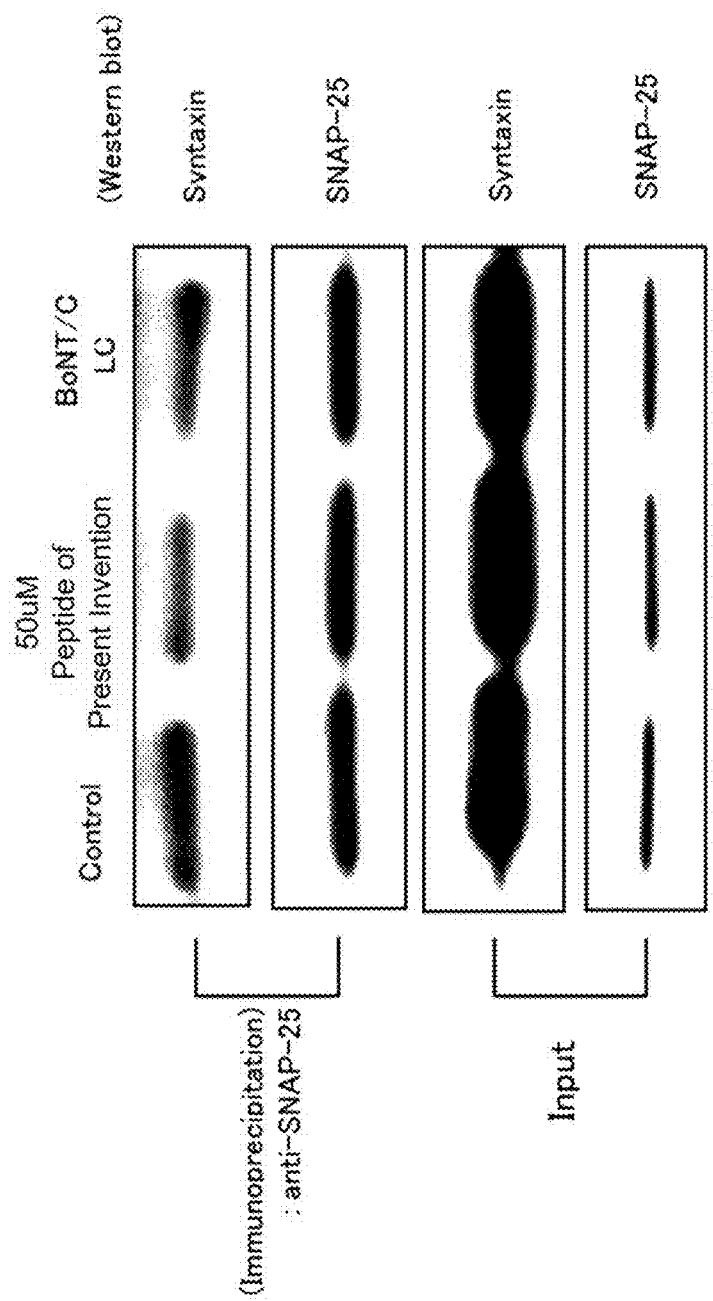

[Figure 7]
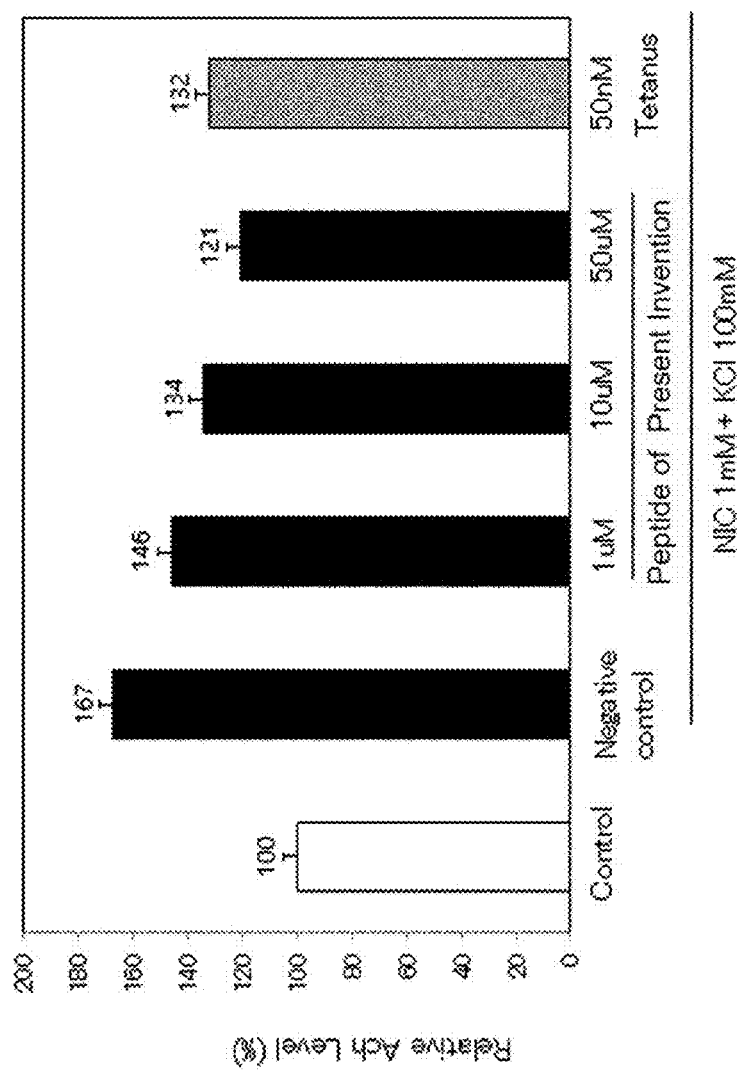

[Figure 8]
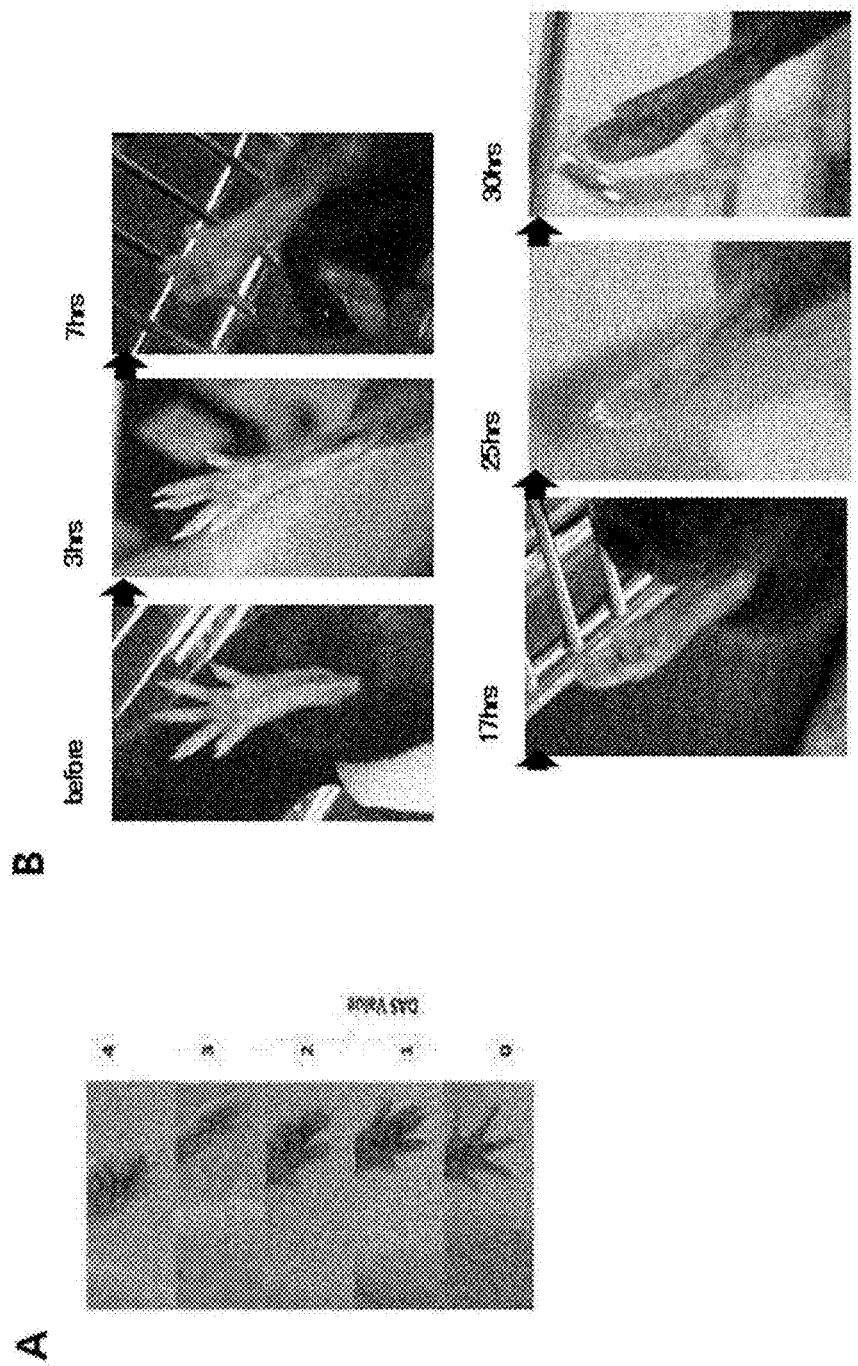

[Figure 9]
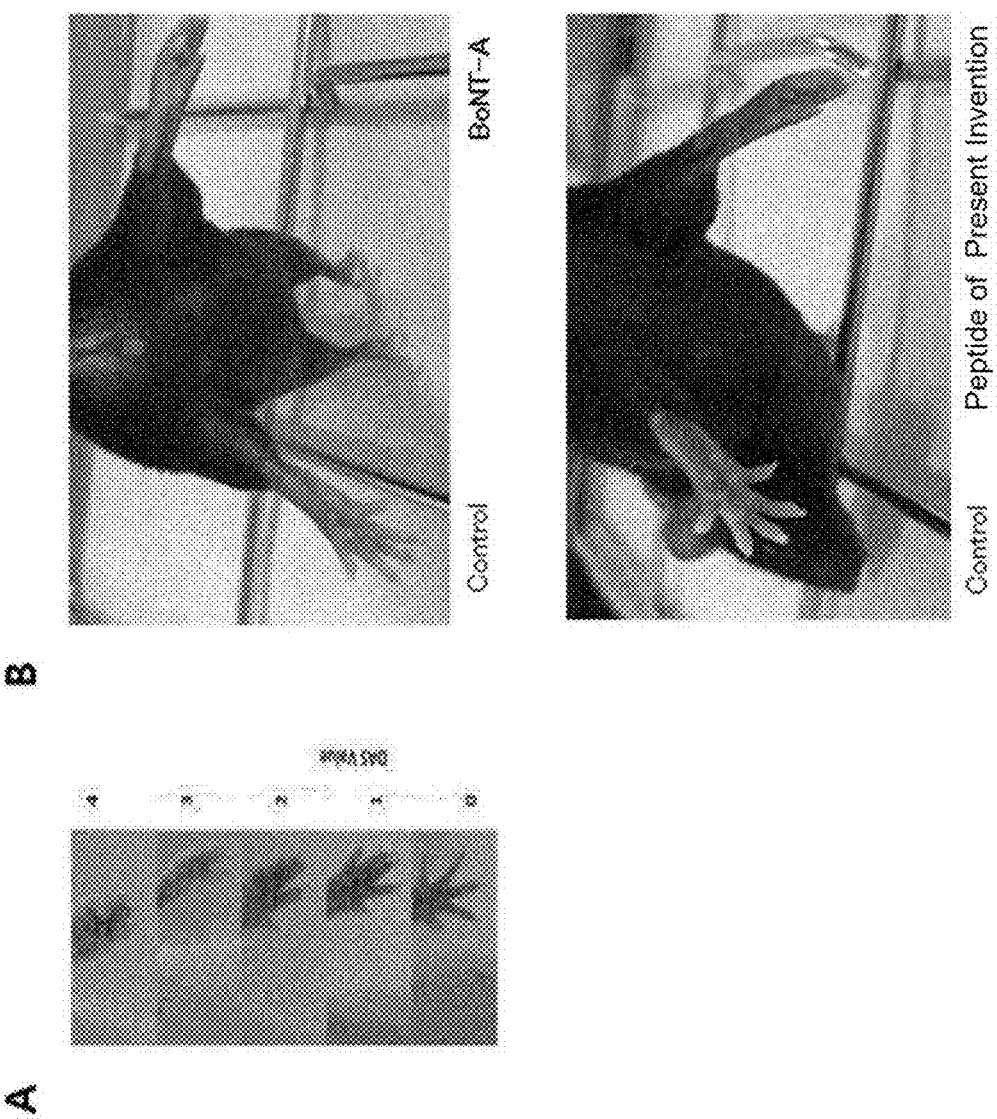

[Figure 10]
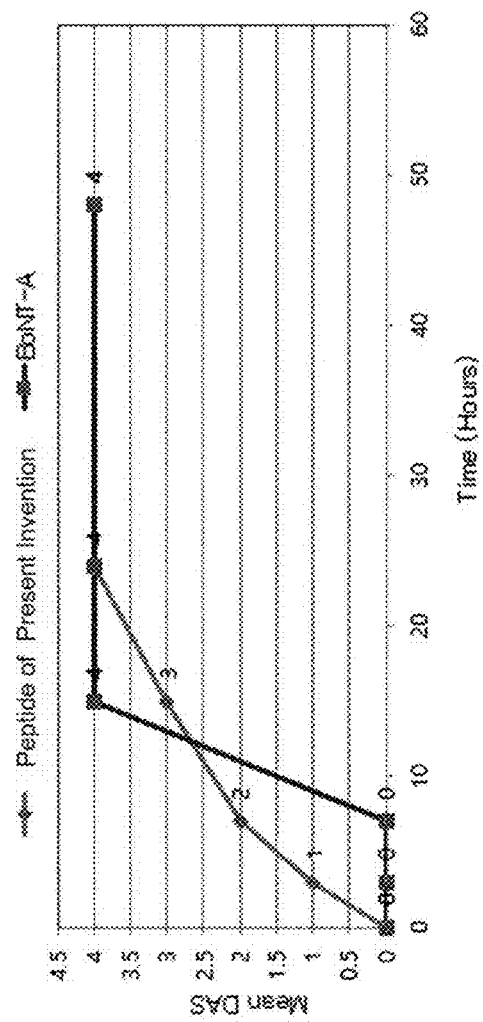

[Figure 11]
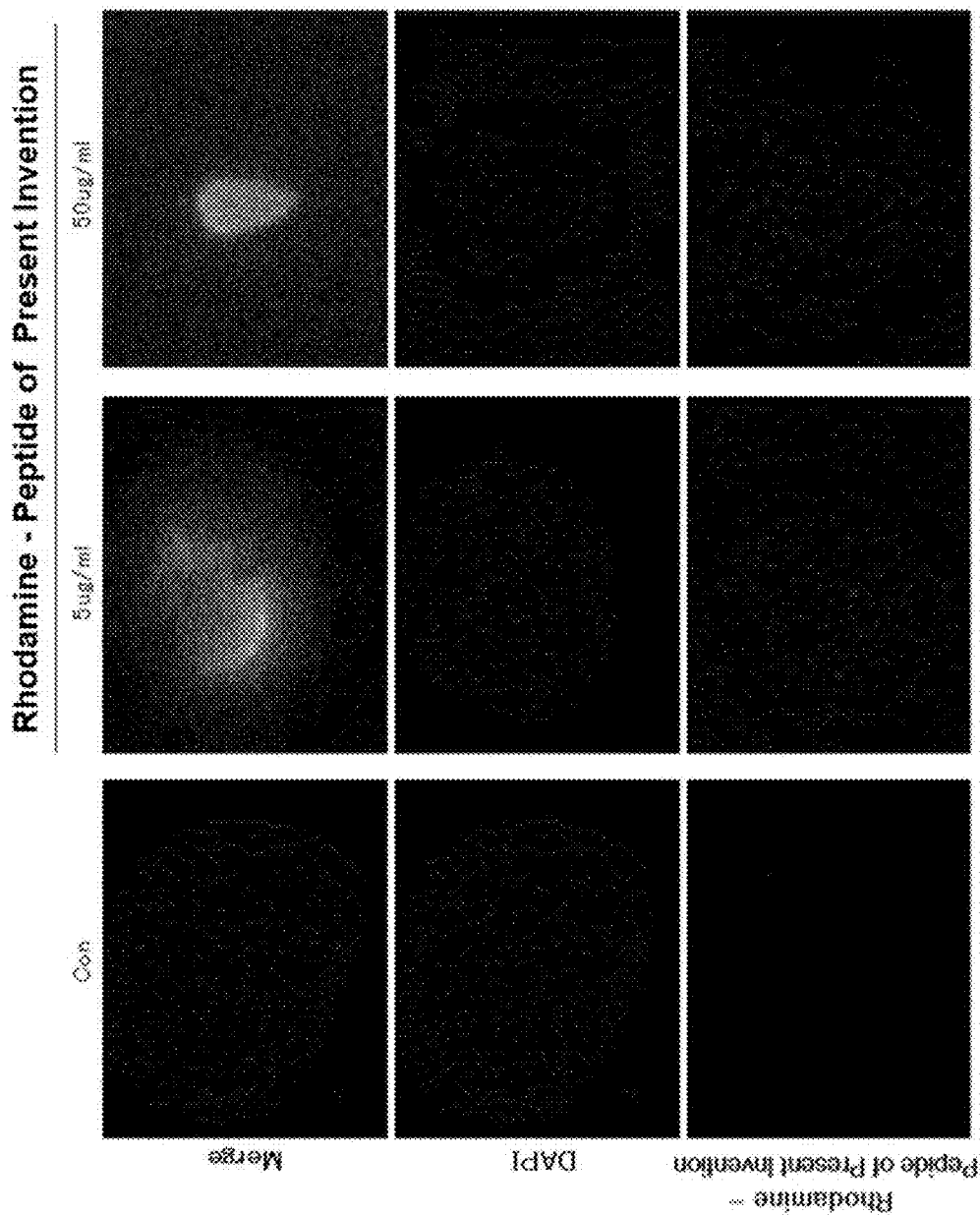

[Figure 12]
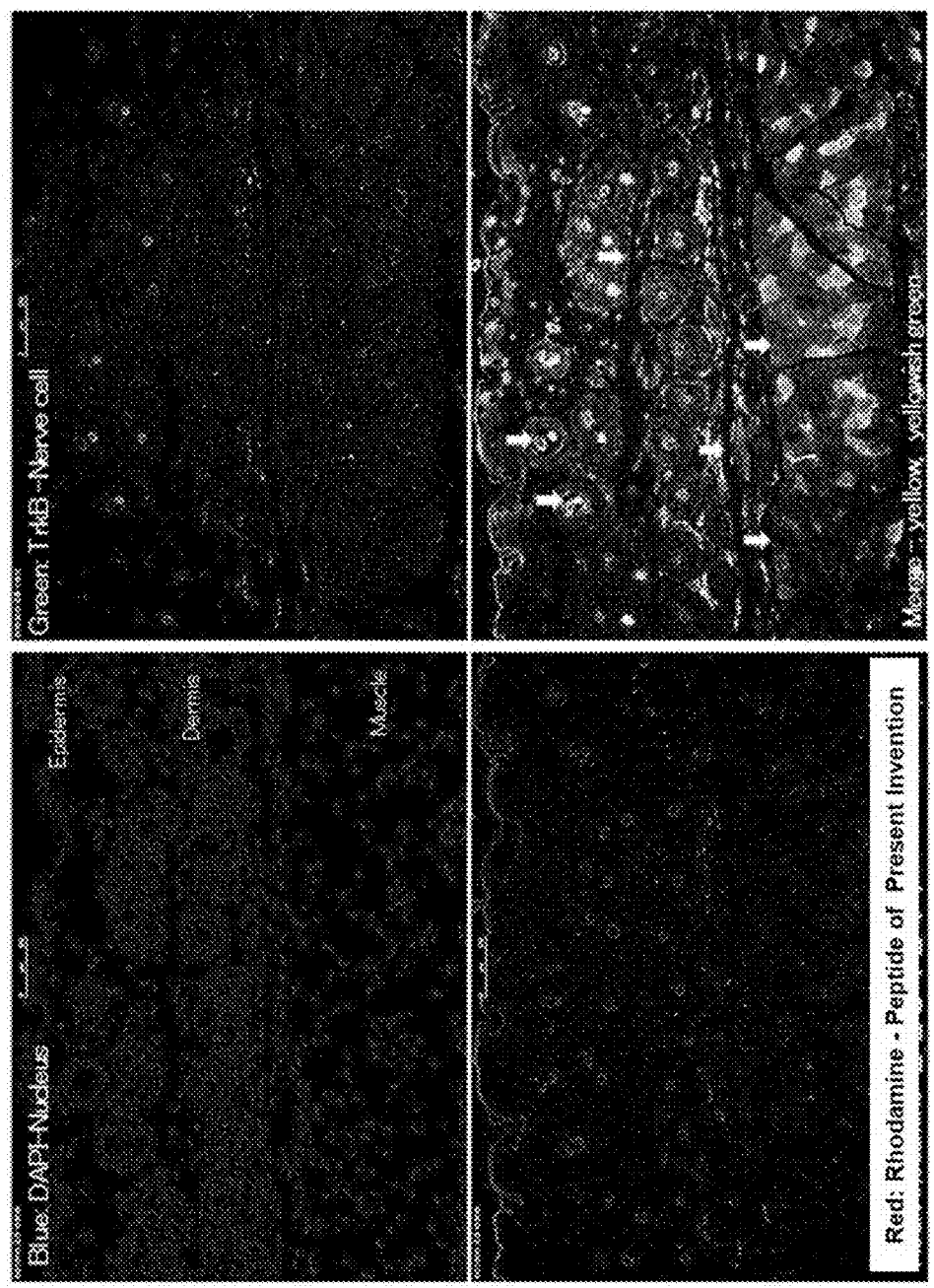

[Figure 13]
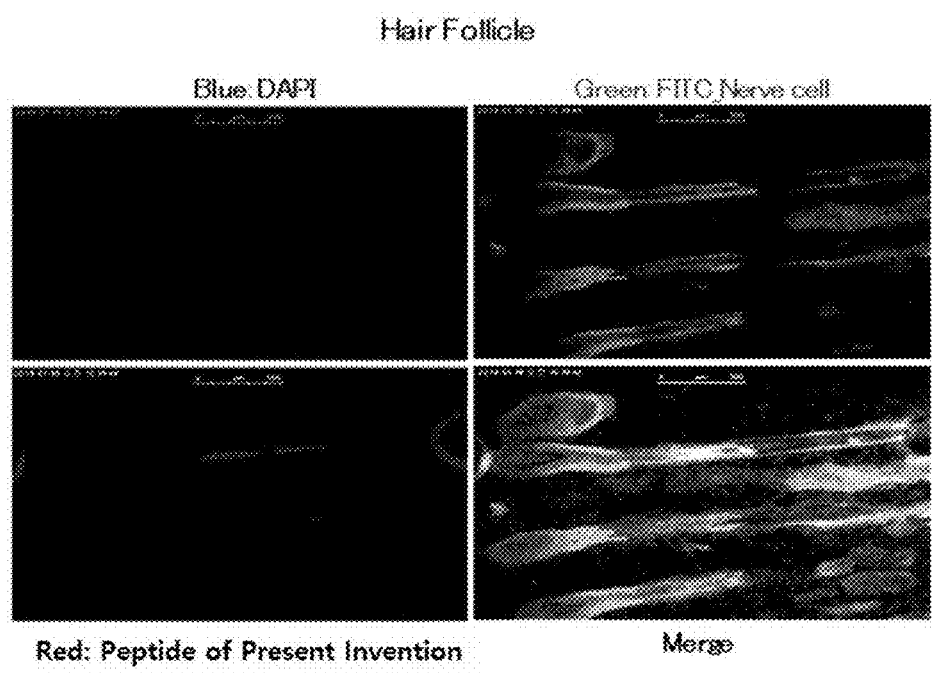

[Figure 14]
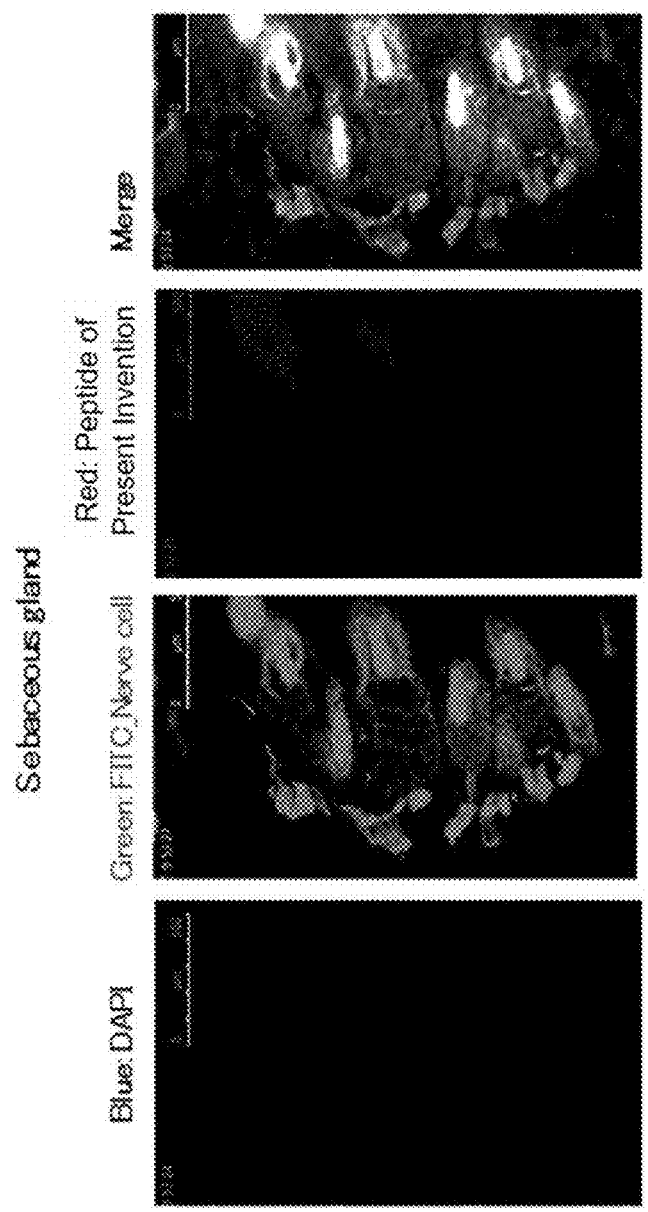

[Figure 15]
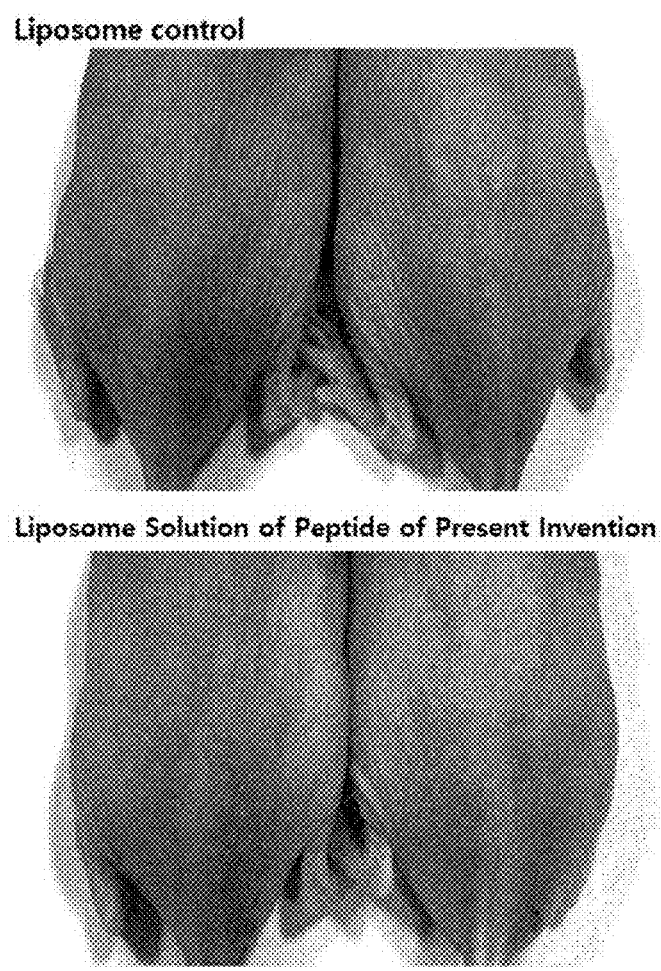

[Figure 16]
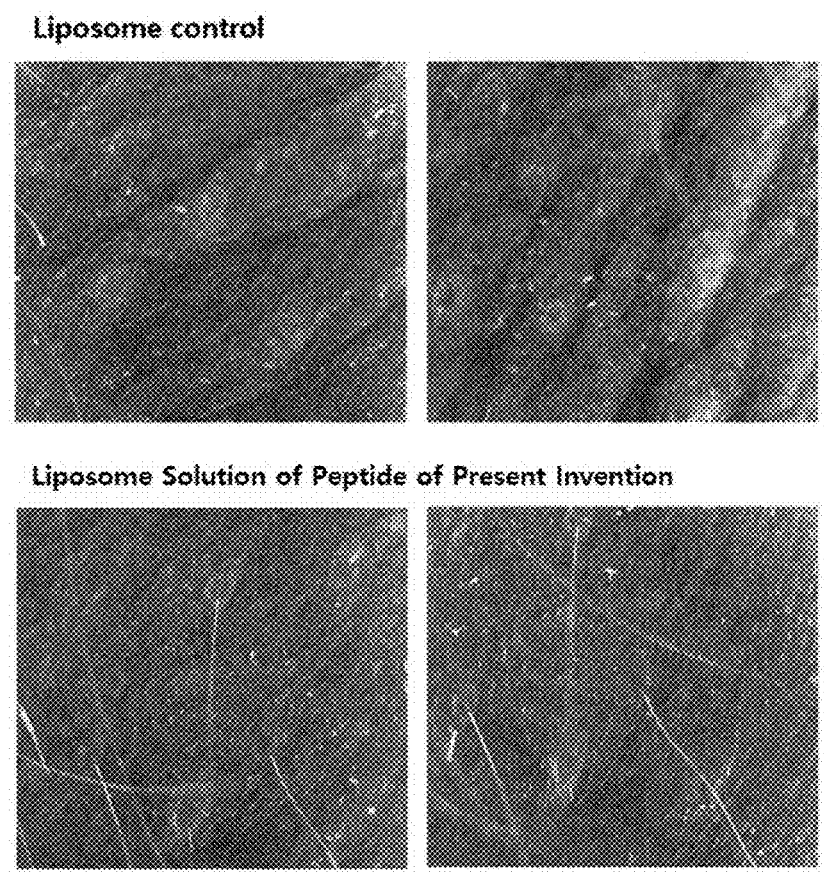

[Figure 17]
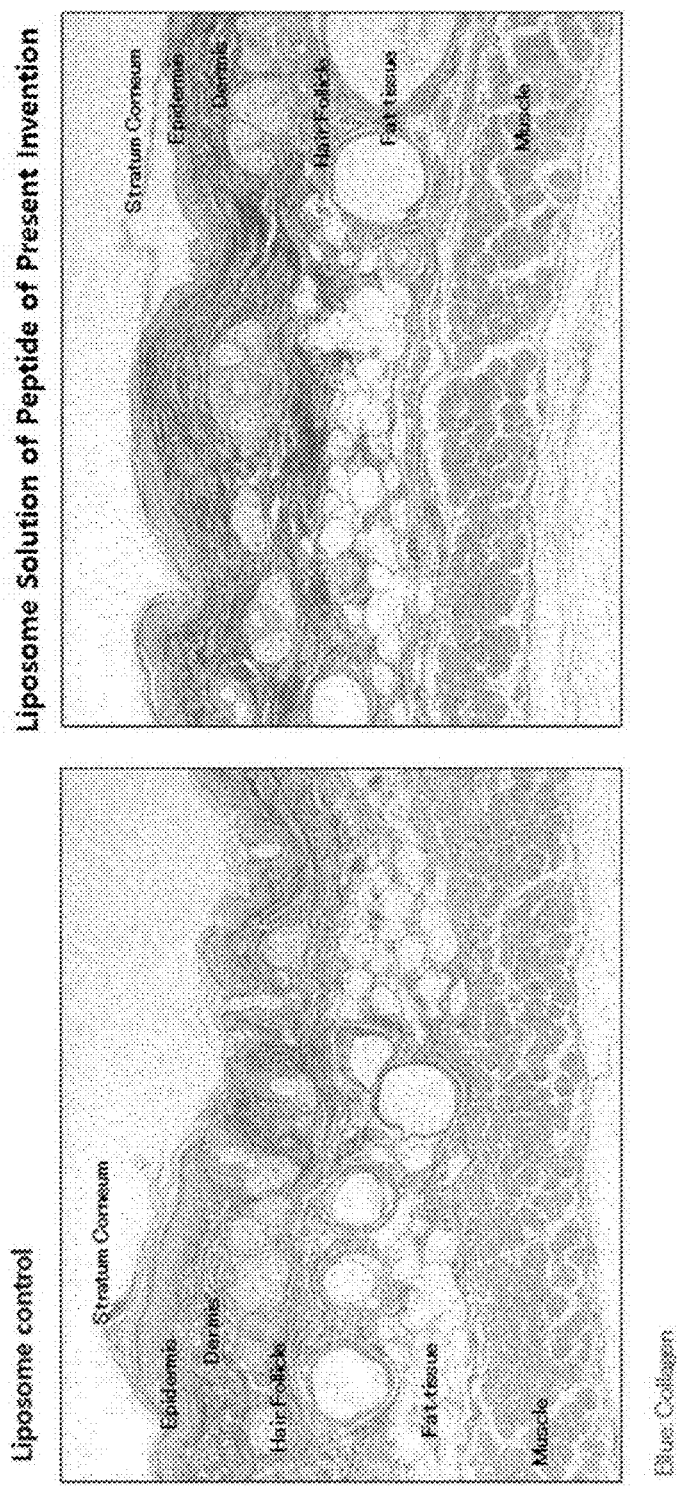

[Figure 18]
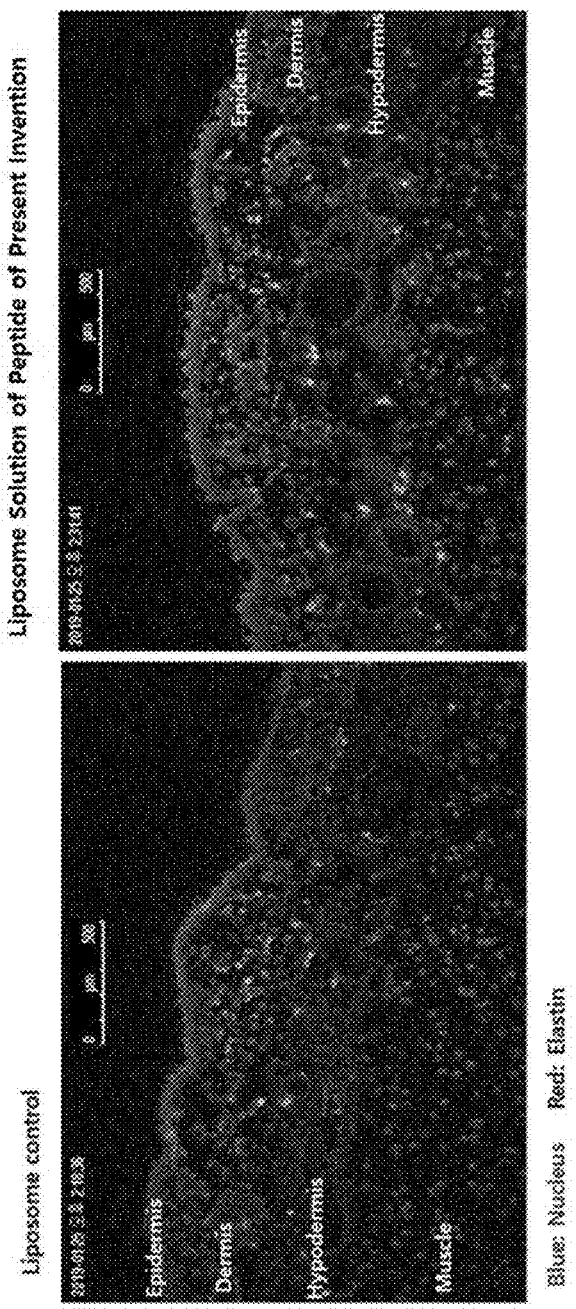

[Figure 19]
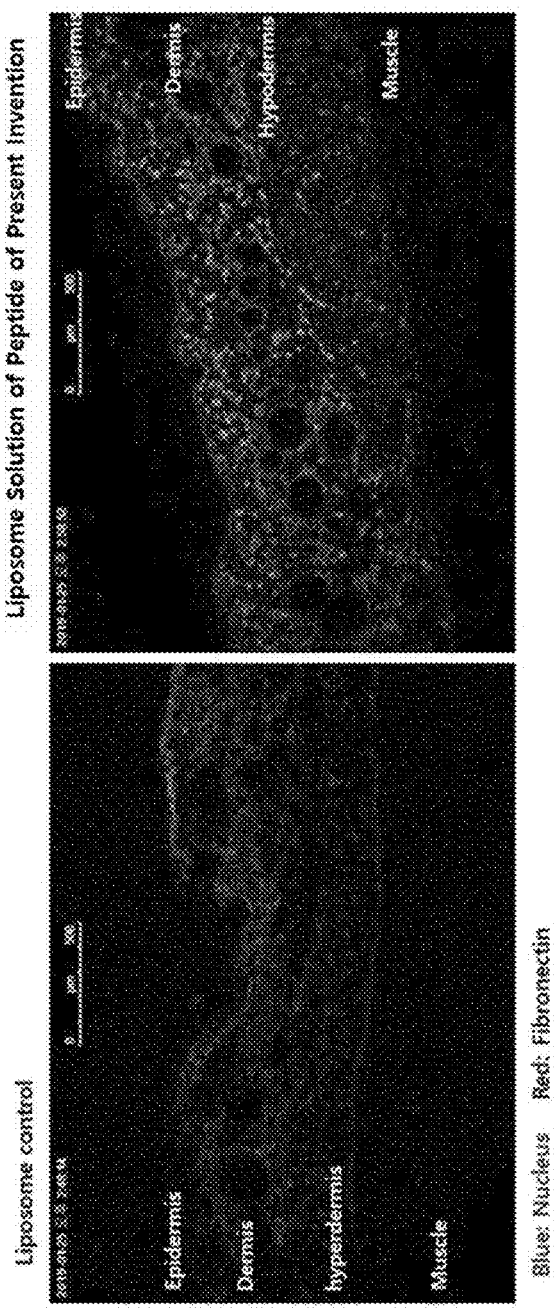

[Figure 20]
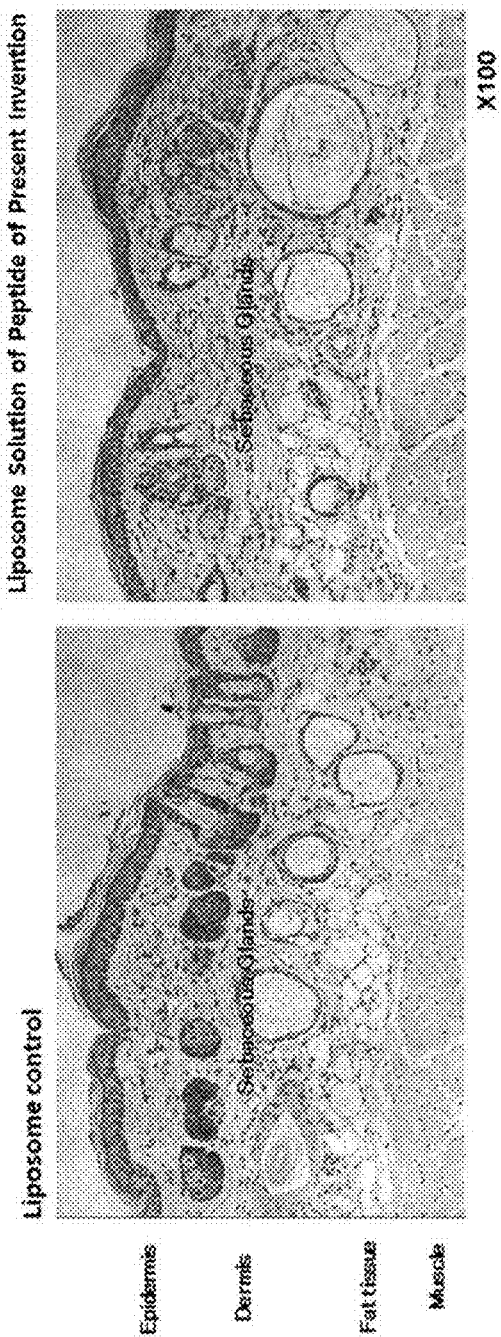

```
                              SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: peptide having physiological activity

<400> SEQUENCE: 1

Lys Phe Leu Ile Lys
1               5
```

COMPOSITION FOR MUSCLE RELAXATION

This application is a National Stage Application of PCT/KR2019/013916, filed 22 Oct. 2019, which claims benefit of Patent Application Serial No. 10-2018-0169495, filed 26 Dec. 2018 in Korea and Patent Application Serial No. 10-2019-0083008, filed 10 Jul. 2019 in Korea and which applications are incorporated herein by reference. To the extent appropriate, a claim of priority is made to each of the above-disclosed applications.

TECHNICAL FIELD

The present invention relates to a peptide having physiological activities and a composition including the same, and more particularly, to a composition (for example, a pharmaceutical composition or a cosmetic composition) for muscle relaxation or for improving skin wrinkles, suppressing sebum production or ameliorating acne, which includes the peptide having physiological activities.

BACKGROUND ART

Neurons (i.e., nerve cells) constituting the nervous system of an animal have axons having a peculiar structure which cannot be found in other cells. An axon has a slender, long structure that projects from the nerve cell body so that the axon is connected to a target of a neuron, through which signals are transduced and substances are transmitted.

A neuromuscular synapse has a specifically differentiated synaptic structure in which terminals of axons are synaptically connected to skeletal muscle cells to transduce impulses from the neurons to muscles. Axons directed to the skeletal muscles are myelinated axons surrounded by the myelin, and branched into various terminal dendrites as the axons get near to the muscles. The branched axons are surrounded by the myelin, but the myelin disappears at the sites of the axons that enter the muscles. In this case, the branched axons form terminal boutons like the axon terminals constituting other synapses, and the terminal boutons are positioned on surfaces of depressed muscle cells. Such a structure is referred to as a 'motor endplate' or a 'neuromuscular synapse.'

As in the other synapses, there are numbers of mitochondria and synaptic vesicles at the axon terminals of the neuromuscular synapses. The synaptic vesicles of the neuromuscular synapses contain acetylcholine as a neurotransmitter. SNARE molecules are essential for the acetylcholine release, and the suppression of an acetylcholine release action causes flaccid palsy. There are synaptic clefts between the axon terminals and muscles, and cell membranes of the skeletal muscle cells serving as post-synaptic parts are depressed toward the sarcoplasm to form a number of junctional folds. Because an acetylcholine receptor is present at the cell membranes around the junctional folds, this structure is supposed to serve to widen an area in which the receptor can be bound to acetylcholine.

When the nerve impulses are transmitted to a neuromuscular synapse, voltage sensitive calcium channels of the terminal cell membrane are opened up so that calcium ions enter the calcium channels. As a result, the synaptic vesicles are fused to the cell membrane to free acetylcholine in the vesicles into synaptic clefts. The freed acetylcholine is allowed to bind to an acetylcholine receptor present in the muscle cell membrane, and thus sodium channels are opened up, thereby causing depolarization of the cell membrane. The impulses starting from the neuromuscular synapse are spread on the surfaces of muscle fibers, and transmitted to the deep parts of muscle cells. The impulses are transmitted to the triads to open membrane calcium channels of the sarcoplasmic reticulum and free calcium ions into the sarcoplasm. Calcium ions are bound to troponin C, and thus the muscles start to contract. When the impulses are interrupted, the calcium ions return to the cisternae of the sarcoplasmic reticulum by means of the active transport, thereby causing the muscle relaxation. Therefore, when the secretion of acetylcholine from the neuromuscular synapse is suppressed, the impulses generated at the neuromuscular synapse are not transmitted to the muscles. In this case, because the impulses are interrupted, the muscles are relaxed.

Meanwhile, a cause of formation of facial expression wrinkles or a mechanism thereof depends on the tension of epidermal muscles pulling the skin in an internal direction. Such muscle tension results from weakened facial muscles, and excessive neuronal activity. The excessive neuronal activity is characterized by the uncontrolled, excessive release of neurotransmitters which give stimulus to muscle fibers. As a result, the molecules serving to control the release of the neurotransmitters relax the tension of muscles to contribute to removal of facial wrinkles. Therefore, there is a need for novel active ingredients that are effective in controlling the release of the neurotransmitters to treat a muscle spasm and in reducing or removing facial asymmetry and/or facial wrinkles (especially, facial expression wrinkles).

*Botulinum* toxin is known to be associated with an action of muscle relaxation. The *Botulinum* toxin is the most commonly used for clinical tests and cosmetics for the purpose of removing facial wrinkles. The *Botulinum* toxin causes a functional damage to a SNARE protein, and has a muscle relaxation effect by interrupting a SNARE complex to inhibit secretion of a neurotransmitter (i.e., acetylcholine).

The *Botulinum* toxin has been used as a muscle relaxant (Korean Patent Publication No. 2010-0020972), or has been used to reduce wrinkles through the use of the muscle relaxation effect of the *Botulinum* toxin. However, because a paralytic effect of the *Botulinum* toxin is reversible for an average of 6 months, such treatment requires repeated injection of the *Botulinum* toxin. Also, because the *Botulinum* toxin has a size recognizable by the patient's immune system, the *Botulinum* toxin may induce an immune response to drugs. Because formation of antibodies against the *Botulinum* toxin results in significant loss in therapeutic efficacy, this is a serious problem. Therefore, there is a need for development of molecules exhibiting a paralytic effect similar to the *Botulinum* toxin, which have more simple and stable molecular structures, which do not induce an immune response, and are effective in terms of the manufacturing cost.

Meanwhile, sebum is produced in sebaceous glands and released through the skin's pores, and has antibacterial and cytostatic actions by forming pellicles on the surfaces of skin and hair to protect our bodies from the invading microbes. The pores are enlarged when the sebum is increasingly secreted from the sebaceous glands or a problem occurs while passing the sebum through the pores. The sebum is accumulated in such enlarged pores, and this sebum is further accumulated while getting tangled with dead skin cells, makeup cosmetic wastes, or dusts. The tangled sebum wastes are oxidized through the contact with radicals in the air, and thus turn brown or black, thereby causing a black head. Also, because the sebum induces acne, there is a need for development of materials capable of suppressing excessive production of sebum.

DISCLOSURE

Technical Problem

Therefore, an object of the present invention is to provide a peptide having various physiological activities such as muscle relaxation, skin wrinkle improvement, sebum production suppression, or acne amelioration, and a pharmaceutical or cosmetic composition including the same.

Technical Solution

To achieve the objects, according to one aspect of the present invention, there is provided a peptide including an amino acid sequence set forth in SEQ ID NO: 1.

According to another aspect of the present invention, there is provided a composition for muscle relaxation including as an active ingredient the peptide including the amino acid sequence set forth in SEQ ID NO: 1.

According to one embodiment of the present invention, the composition may be in the form of a pharmaceutical composition or a cosmetic composition, but the present invention is not limited thereto.

According to another embodiment of the present invention, the peptide may be included at a content of 0.001% by weight to 60% by weight, based on 100% by weight of the composition for muscle relaxation, but the present invention is not limited thereto.

According to still another embodiment of the present invention, the composition may be used to prevent or treat a neuromuscular disease. In one preferred embodiment of the present invention, the neuromuscular disease may include eyelid twitching, torticollis, cervical dystonia, tonic blepharospasm, axillary hyperhidrosis, anal fissure, colpospasm, achalasia, a headache disorder, idiopathic and neurogenic detrusor overactivity, focal dystonia, temporomandibular joint pain/disorder, diabetic neuropathy, vocal cord dysfunction, strabismus, chronic neuropathy, facial muscular hypertrophy, detrusor-sphincter dyssynergia, or benign prostatic hyperplasia, and the headache disorder may be migraine, but the present invention is not limited thereto.

According to yet another embodiment of the present invention, the peptide may inhibit secretion of acetylcholine.

According to yet another aspect of the present invention, there is provided a cosmetic composition including as the active ingredient the peptide including the amino acid sequence set forth in SEQ ID NO: 1.

According to one embodiment of the present invention, the cosmetic composition may be used for the purpose of improving skin conditions, for example, improving skin wrinkles, suppressing sebum production, or ameliorating acne, but the present invention is not limited thereto.

According to another embodiment of the present invention, the peptide may be included at a content of 0.001% by weight to 60% by weight, based on 100% by weight of the cosmetic composition, but the present invention is not limited thereto.

According to yet another embodiment of the present invention, the peptide may increase expression of collagen, but the present invention is not limited thereto.

Advantageous Effects

Because the peptide including an amino acid sequence set forth in SEQ ID NO: 1 according to the present invention has physiological activities such as muscle relaxation, skin wrinkle improvement, sebum production suppression, and the like, the peptide can be used as an active ingredient in a composition for muscle relaxation, a composition for improving skin wrinkles, a composition for suppressing sebum production, a composition for suppressing generation of a black head, or a composition for ameliorating acne.

DESCRIPTION OF DRAWINGS

FIG. 1 shows the results of evaluating the high-temperature stability of a peptide including an amino acid sequence set forth in SEQ ID NO: 1 when stored for a long period of time.

FIG. 2 shows the results of evaluating the high-temperature stability the peptide including the amino acid sequence set forth in SEQ ID NO: 1.

FIG. 3 shows a decomposition degree of recombinant syntaxin 1A by the peptide including the amino acid sequence set forth in SEQ ID NO: 1.

FIG. 4 shows a decomposition degree of endogenous syntaxin 1A by the peptide including the amino acid sequence set forth in SEQ ID NO: 1.

FIG. 5 shows an inhibitory effect of the peptide including the amino acid sequence set forth in SEQ ID NO: 1 on formation of a SNARE complex.

FIG. 6 shows an inhibitory effect of the peptide including the amino acid sequence set forth in SEQ ID NO: 1 on formation of the SNARE complex.

FIG. 7 is a graph showing an inhibitory effect of the peptide including the amino acid sequence set forth in SEQ ID NO: 1 on secretion of acetylcholine.

FIG. 8 shows a muscle relaxation effect of the peptide including the amino acid sequence set forth in SEQ ID NO: 1.

FIGS. 9 and 10 shows the results of comparing muscle relaxation effects of Botox and the peptide including the amino acid sequence set forth in SEQ ID NO: 1.

FIG. 11 shows the results of determining whether the peptide including the amino acid sequence set forth in SEQ ID NO: 1 penetrates into cells.

FIG. 12 shows the results of verifying a tissue penetration pattern of the peptide including the amino acid sequence set forth in SEQ ID NO: 1.

FIG. 13 shows the results of verifying that the tissue penetration pattern of the peptide including the amino acid sequence set forth in SEQ ID NO: 1 are present around the hair follicle.

FIG. 14 shows the results of verifying that the tissue penetration pattern of the peptide including the amino acid sequence set forth in SEQ ID NO: 1 are present around the sebaceous glands.

FIGS. 15 and 16 show a wrinkle-reducing effect of the peptide including the amino acid sequence set forth in SEQ ID NO: 1.

FIG. 17 shows an increased level of collagen in applying the peptide including the amino acid sequence set forth in SEQ ID NO: 1.

FIG. 18 shows an increased level of elastin in applying the peptide including the amino acid sequence set forth in SEQ ID NO: 1.

FIG. 19 shows an increased level of fibronectin in applying the peptide including the amino acid sequence set forth in SEQ ID NO: 1.

FIG. 20 shows the results of a decrease in the number of sebaceous glands and a decrease in expression of a marker associated with the sebum production in applying the peptide including the amino acid sequence set forth in SEQ ID NO: 1.

BEST MODE

Hereinafter, the present invention will be described in detail.

1: Peptide of the Present Invention

The present invention provides a peptide having useful physiological activities, for example, various physiological activities such as muscle relaxation, skin wrinkle improvement, sebum production suppression, or acne amelioration.

The peptide of the present invention includes an amino acid sequence set forth in SEQ ID NO: 1. According to one embodiment, the peptide of the present invention may consist of an amino acid sequence set forth in SEQ ID NO: 1, but the present invention is not limited thereto.

In this specification, the term "peptide" refers to a linear molecule formed by allowing amino acid residues to bind to each other via peptide bonds. The peptide may be prepared using conventional biological or chemical synthesis methods known in the related art, particularly, solid-phase synthesis techniques.

The peptide may include variants or fragments with amino acids, which have different sequences within an extent having no effect on the functionalities thereof due to deletion, insertion, or substitution of an amino acid residue(s), or a combination thereof. The replacement of amino acids without varying the activity of the peptide as a whole is known in the related art. In certain cases, the peptide may be modified by phosphorylation, sulfation, acrylation, glycosylation, methylation, farnesylation, and the like. Therefore, the present invention includes a peptide, which has substantially the same amino acid sequence as the peptide including the amino acid sequence set forth in SEQ ID NO: 1, and variants or active fragments thereof. The expression "substantially identical protein" refers to a protein that has an amino acid sequence having a sequence homology of 60% or more, preferably 75% or more, for example, 80% or more, 90% or more, 95% or more, 98% or more, or 99% or more with respect to the amino acid sequence of SEQ ID NO: 1, but the present invention is not limited thereto. Proteins having an amino acid sequence homology of 60% or more and exhibiting the same activities fall within the scope of the present invention. Also, the peptide of the present invention may further include a targeted sequence, a tag, a labeled residue, or an amino acid sequence prepared for the special purpose of enhancing the half-life or stability of the peptide.

Also, the peptide of the present invention may be obtained using various methods well known in the related art. According to one embodiment of the present invention, the peptide of the present invention may be prepared using polynucleotide recombination and a protein expression system, or may be prepared using a method of synthesizing a peptide in vitro by means of chemical synthesis such as peptide synthesis, and a cell-free protein synthesis method, and the like.

In addition, a protecting group may be bound to the N- or C-terminus of the peptide of the present invention in order to realize higher chemical stability, enhanced pharmacological properties (half-life, absorptivity, titration, efficacy, and the like), modified specificity (for example, a broad range of biologically active spectra), and reduced antigenicity. For example, the protecting group may be an acetyl group, a fluorenylmethoxycarbonyl group, a formyl group, a palmitoyl group, a myristyl group, a stearyl group, or polyethylene glycol (PEG). However, protecting groups may be used without limitation as long as the protecting groups can modify the peptide, particularly can enhance the stability of the peptide. The term "stability" is used as a meaning including in vivo stability in which the peptide of the present invention is protected from the attack of in vivo protein-cutting enzymes, as well as storage stability (for example, room-temperature storage stability).

2: Pharmaceutical Composition Including Peptide of the Present Invention

Another aspect of the present invention provides a pharmaceutical composition for muscle relaxation including the peptide including the amino acid sequence set forth in SEQ ID NO: 1.

Because the peptide including the amino acid sequence of SEQ ID NO: 1 is identical to the peptide as described in the section "1: Peptide of the present invention," see the section "1: Peptide of the present invention" for a specific description thereof. Hereinafter, only a specific configuration of the pharmaceutical composition will be described.

According to one embodiment of the present invention, the peptide of the present invention has a muscle relaxation activity, and thus may be used as an active ingredient of a composition for muscle relaxation. Accordingly, the present invention provides a pharmaceutical composition for muscle relaxation, which includes as the active ingredient the peptide including the amino acid sequence set forth in SEQ ID NO: 1.

The peptide may be included at a content of 0.001% by weight to 60% by weight, for example, a content of 0.01% by weight to 50% by weight, based on 100% by weight of the pharmaceutical composition for muscle relaxation. When the content of the peptide in the pharmaceutical composition for muscle relaxation is less than the lower limit, a muscle relaxation effect of the peptide may be not sufficiently expressed. On the other hand, when the content of the peptide is greater than the upper limit, a relatively low effect of the peptide may be obtained with respect to the concentration of the peptide added.

The pharmaceutical composition of the present invention may be used to prevent or treat a neuromuscular disease. In this case, the pharmaceutical composition of the present invention may be unlimitedly applied to the neuromuscular disease as long as the neuromuscular disease is a disease to be treated for the purpose of muscle relaxation.

The term "protection" used in the present invention refers to all types of actions in which the pharmaceutical composition of the present invention delays the onset of the neuromuscular disease.

The term "inhibition" used in the present invention refers to all types of actions in which the pharmaceutical composition of the present invention reduces the onset of the neuromuscular disease.

The term "treatment" used in the present invention refers to all types of actions in which the pharmaceutical composition of the present invention improves or ameliorates the symptoms of the neuromuscular disease.

The term "administration" used in the present invention refers to the introduction of a certain material into a subject using any proper methods. In this case, the pharmaceutical composition of the present invention may be administered through any common routes of administration through which the composition may reach an in vivo target. A route of administration of the pharmaceutical composition of the present invention is not particularly limited, but the pharmaceutical composition of the present invention may be administered orally or parenterally. Particularly, the pharmaceutical composition of the present invention may be administered parenterally, and, more particularly, may be administered by applying the composition on the skin (i.e., dermal administration). Particularly, the administration of the pharmaceutical composition of the present invention may be performed once to four times a day, twice to three times a day, or twice a day. Also, the administration of the pharmaceutical composition of the present invention may be performed for a period of 4 weeks or more, 8 weeks or more, 4 weeks to 12 weeks, or 8 weeks to 12 weeks.

The term "neuromuscular disease" used in the present invention refers to a disorder which occurs in the peripheral nerves and muscles. A peripheral nerve refers to a neural network which diverges from the central nervous system in the skull or the spine to connect end organs such as muscles or skin to the central nervous system, and serves to transmit commends made in the central nervous system to the end organs such as muscles, or transmit sensory information such as a sense of pain to the central nervous system. A disorder of the peripheral nervous system includes peripheral nerve dysfunction, diseases caused in the neuromuscular synapses in which the peripheral nerves are connected to the muscles, or the muscles themselves, and the like.

Non-limiting examples of the neuromuscular disease include diseases such as eyelid twitching, torticollis (an unnatural neck posture in which the neck is tilted to one side due to the contraction of muscles), cervical dystonia, tonic blepharospasm, axillary hyperhidrosis, anal fissure, colpospasm, achalasia, a headache disorder, idiopathic and neurogenic detrusor overactivity, focal dystonia (in limbs, temporomandibular joints, vocal cords, and the like), temporomandibular joint pain/disorder, diabetic neuropathy, vocal cord dysfunction, strabismus, chronic neuropathy, facial muscular hypertrophy (in masticatory muscles, and the like), detrusor-sphincter dyssynergia, benign prostatic hyperplasia, and the like. The headache disorder may be migraine.

According to one embodiment of the present invention, the pharmaceutical composition of the present invention may further include a proper carrier, excipient or diluent, which is commonly used to prepare the pharmaceutical composition.

The carrier, excipient or diluent that may be used in the pharmaceutical composition of the present invention includes lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methyl hydroxybenzoate, propyl hydroxybenzoate, talc, magnesium stearate, mineral oil, and the like.

The pharmaceutical composition of the present invention may be used for formulation into forms such as powders, granules, tablets, capsules, suspensions, emulsions, syrup, oral formulations (such as aerosol), preparations for external use, suppositories and sterile injectable solutions, depending on the conventional methods used.

When formulated, the pharmaceutical composition may be prepared using a diluent or an excipient generally used in the art, such as a filler, an extending agent, a binding agent, a wetting agent, a disintegrating agent, a surfactant, and the like. A solid preparation for oral administration includes a tablet, a pill, a powder, a granule, a capsule, and the like. Such a solid preparation may be prepared by mixing the compound with at least one excipient, for example, starch, calcium carbonate, sucrose or lactose, gelatin, and the like. Also, in addition to the simple excipients, lubricants such as magnesium stearate, talc, and the like may be used herein.

A liquid phase preparation for oral administration includes a suspension, a solution for internal use, an emulsion, a syrup, and the like. Such a liquid phase preparation may encompass various excipients, for example, a wetting agent, a sweetening agent, a flavoring agent, a preservative, and the like in addition to the inert diluents (for example, water, liquid paraffin) commonly used in the art.

A preparation for parenteral administration includes a sterile aqueous solution, a non-aqueous solvent, a suspension, an emulsion, a lyophilized preparation, a suppository, and the like. A vegetable oil such as propylene glycol, polyethylene glycol, or olive oil, or an injectable ester such as ethyl oleate, and the like may be used as the non-aqueous solvent and the suspension. Witepsol, Macrogol, Tween 61, cocoa butter, laurin butter, glycerol gelatin, and the like may be used as a base of the suppository.

A solid preparation for oral administration includes a tablet, a pill, a powder, a granule, a capsule, and the like. Such a solid preparation may be prepared by mixing the pharmaceutical composition of the present invention with at least one excipient, for example, starch, calcium carbonate, sucrose, lactose, gelatin, and the like. In addition to the simple excipients, lubricants such as magnesium stearate, talc, and the like may also be used herein.

A liquid phase preparation for oral administration includes a suspension, a solution for internal use, an emulsion, a syrup, and the like. Such a liquid phase preparation may encompass various excipients, for example, a wetting agent, a sweetening agent, a flavoring agent, a preservative, and the like in addition to the inert diluents (for example, water, liquid paraffin) commonly used in the art.

A preparation for application onto the skin includes a dusting powder, an emulsion, suspension, an oil, a spray, an ointment, a cream paste, a gel, a foam, or a solution. The pharmaceutical preparation of the present invention may be an anhydrous ointment, and may contain paraffin that is suitable for local application and is in a liquid state at a body temperature, particularly, low-viscosity paraffin, or may contain the natural fats or partially synthesized fats, for example, coconut fatty acid triglyceride, hydrogenated oil (for example, hydrogenated peanut oil or Caster oil), partial fatty acid ester of glycerol (for example, glycerol monostearate and distearate), silicone (for example, polymethylsiloxane such as hexamethyldisiloxane or octamethyltrisiloxane), and the like. For example, the pharmaceutical preparation may contain a fatty alcohol, which is associated with an aqueous cream and serves to increase the moisture absorption capability, and sterols, wool wax, other emulsifying agents and/or other additives.

The dose of the peptide including the amino acid sequence, which is contained in the pharmaceutical composition of the present invention may vary depending on the condition and weight of a patient, the severity of a disease, the form of a drug, a route of administration, and an administration time, but may be properly chosen, when necessary. For example, the peptide including the amino acid sequence may be administered daily at a dose of 0.0001 to 1,000 mg/kg, particularly a dose of 0.1 to 1,000 mg/kg. The peptide may be applied once a day, or applied in several divided doses. However, the scope of the present invention is not limited by the dose of the pharmaceutical composition. The dose of the peptide including the amino acid sequence according to the present invention may fluctuate depending on a route of administration, the severity of a disease, the gender, weight, and age of a patient, and the like. Therefore, the dose of the peptide is not intended to limit the scope of the present invention in some ways.

The pharmaceutical composition of the present invention may be administered to mammals (for example, mice, rats, livestock, humans, and the like) through various routes of administration. A mode of administration may be expected. In this case, the peptide may, for example, be administered through all modes of administration such as oral, rectal or intravenous, intramuscular, subcutaneous, intrauterine dural, or intracerebroventricular injection.

In addition to the peptide including the amino acid sequence, the pharmaceutical composition for preventing, inhibiting or treating a neuromuscular disease according to the present invention may further include one or more active ingredient having an effect of improving, ameliorating or preventing the neuromuscular disease.

To improve, ameliorate or prevent the neuromuscular disease, the pharmaceutical composition of the present invention may be used alone or in combination with surgery, hormone therapy, drug treatment, and other therapies using a biological response modifier.

According to one embodiment of the present invention, the peptide of the present invention is stable at a high temperature (see FIGS. 1 and 2), decomposes syntaxin 1A that participates in the release of neurotransmitters, suppresses formation of a SNARE complex (see FIGS. 3 to 6), inhibits secretion of acetylcholine (see FIG. 7), has a muscle relaxation effect (see FIGS. 8 to 10), is penetrable into the cells, and penetrates to the tunica muscularis of a tissue to coexist with a neuronal marker, thereby exhibiting a muscle relaxation effect (see FIGS. 11 to 14).

3: Cosmetic Composition Including Peptide of the Present Invention

Still another aspect of the present invention provides a cosmetic composition including as the active ingredient the peptide including the amino acid sequence set forth in SEQ ID NO: 1.

Because the peptide including the amino acid sequence of SEQ ID NO: 1 is identical to the peptide as described in the section "1: Peptide of the present invention," see the section '1: Peptide of the present invention for a specific description thereof. Hereinafter, only a specific configuration of the cosmetic composition will be described.

In the present invention, the term "pores" refers to small holes through which sebum present in a face, a forehead, a nose, and the like is secreted, and the term "black head" refers to sebum that looks black as a mixture of degenerated sebum, old dead skin cells, and the like is accumulated in the pores and contaminants are deposited around the pores.

According to one embodiment of the present invention, the cosmetic composition of the present invention may be a cosmetic composition for improving skin conditions. The term "improvement of skin conditions" may generally mean a process of treating, relieving or alleviating skin damage caused by intrinsic or extrinsic factors of the skin, or an effect thereof. For example, the improvement may mean that the cosmetic composition is used to improve wrinkles, enhance skin elasticity, regenerate wounds, suppress sebum production, or ameliorate acne, and the like, but the present invention is not limited thereto.

According to one embodiment of the present invention, the peptide of the present invention is stable at a high temperature (see FIGS. 1 and 2), and has an effect of improving skin wrinkles due to the muscle relaxation or an increase in dermal components (see FIGS. 15 to 19). The dermal components may include collagen, but the present invention is not limited thereto.

According to one embodiment of the present invention, the peptide of the present invention is stable at a high temperature (see FIGS. 1 and 2), and the number of sebaceous glands is reduced, and an expression level of the sebum production-related marker is lowered (see FIG. 20).

The cosmetic composition of the present invention may be prepared in a liquid or solid form using a base material, an adjuvant, and an additive commonly used in the field of cosmetics. The cosmetics in a liquid or solid form may, for example, include a face lotion, a cream, a bath preparation, and the like, but the present invention is not limited thereto. For example, the base material, adjuvant and additive commonly used in the field of cosmetics include water, alcohol, propylene glycol, stearic acid, glycerol, cetyl alcohol, liquid paraffin, and the like, but the present invention is not particularly limited thereto.

In addition to the peptide including the amino acid sequence, the cosmetic composition of the present invention may include components commonly used in the cosmetic composition. For example, the cosmetic composition may include conventional adjuvants and carriers such as an antioxidant, a stabilizing agent, a solubilizing agent, vitamins, a pigment, and a fragrance.

The cosmetic composition of the present invention may be prepared into any formulations generally obtained in the related art. For example, the cosmetic composition may be formulated to prepare a solution, a suspension, an emulsion, a paste, a gel, a cream, a lotion, a powder, soup, a surfactant-containing cleansing, an oil, a powder foundation, an emulsion foundation, a wax foundation, a spray, and the like, but the present invention is not limited thereto. More specifically, the cosmetic composition may be formulated to prepare a toner, a lotion, a nourishing cream, a massage cream, an essence, an eye cream, a cleansing cream, a cleansing foam, a cleansing water, a pack, a spray, or a powder.

When the formulation of the cosmetic composition of the present invention is a paste, a cream, or a gel, an animal oil, a vegetable oil, wax, paraffin, starch, tragacanth, cellulose derivative, polyethylene glycol, silicone, bentonite, silica, talc, zinc oxide, or the like may be used as the carrier component.

When the formulation of the cosmetic composition of the present invention is a powder or a spray, lactose, talc, silica, aluminum hydroxide, calcium silicate, or a polyamide powder may be used as the carrier component. Particularly, when the formulation is a spray, the formulation may further include a propellant such as chlorofluorohydrocarbon, propane/butane, or dimethyl ether.

When the formulation of the cosmetic composition of the present invention is an emulsion, a solvent, a solubilizing agent, or an emulsifying agent may be used as the carrier component. For example, the carrier component includes water, ethanol, isopropanol, ethyl carbonate, ethyl acetate, benzyl alcohol, benzyl benzoate, propylene glycol, 1,3-butylene glycol oil, glycerol aliphatic ester, polyethylene glycol, or a fatty acid ester of sorbitan.

When the formulation of the cosmetic composition of the present invention is a suspension, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tragacanth, or the like may be used as the carrier component.

When the formulation of the cosmetic composition of the present invention is a surfactant-containing cleansing, aliphatic alcohol sulfate, aliphatic alcohol ether sulfate, sulfosuccinate monoester, an imidazolinium derivative, methyl taurate, sarcosinate, fatty acid amide ether sulfate, alkyl amido betaine, aliphatic alcohol, fatty acid glyceride, fatty acid diethanolamide, vegetable oil, a lanolin derivative, ethoxylated glycerol fatty acid ester, or the like may be used as the carrier component.

The cosmetic composition of the present invention may be used alone, or may be used by double application, or may be used by double application with another cosmetic composition other than the cosmetic composition of the present invention. Also, the cosmetic composition of the present invention, which has an excellent skin-moisturizing effect and an excellent skin barrier-improving effect, may be used according to the conventional methods of use, and its number of usage may vary depending on the user's skin state or preference.

When the cosmetic composition of the present invention is soap, a surfactant-containing cleansing, or a surfactant-free cleansing formulation, the cosmetic composition may be wiped off, detached, or washed with water after applied onto the skin. As a specific example, the soap is liquid soap, soap powder, solid soap, and oil soap, the surfactant-containing cleansing formulation is a cleansing foam, a cleansing water, a cleansing towel, and a cleansing pack, and the surfactant-free cleansing formulation is a cleansing cream, a cleansing lotion, a cleansing water, and a cleansing gel, but the present invention is not limited thereto.

4: Use of Pharmaceutical Composition or Cosmetic Composition Including Peptide of the Present Invention Yet another aspect of the present invention provides the use of the pharmaceutical composition or the cosmetic composition, which includes the peptide including the amino acid sequence set forth in SEQ ID NO: 1.

Because the peptide including the amino acid sequence of SEQ ID NO: 1 is identical to the peptide as described in the section "1: Peptide of the present invention," see the section '1: Peptide of the present invention for a specific description thereof. Hereinafter, only the use of the composition including the peptide will be described.

According to one aspect of the present invention, the present invention provides a method for muscle relaxation, which includes applying the peptide or the pharmaceutical composition to the skin, or the skin in which muscles are contracted. The application may include application to the skin, but the present invention is not limited thereto.

According to another aspect of the present invention, the present invention provides a method of preventing, inhibiting or treating a neuromuscular disease, which includes administering the peptide or the pharmaceutical composition to a subject, or a subject who has developed the neuromuscular disease.

The pharmaceutical composition is as described in the section "2: Pharmaceutical composition including peptide of the present invention."

An effective amount of the peptide including the amino acid sequence of SEQ ID NO: 1, or the pharmaceutical composition including the peptide may be applied/administered to a subject in need thereof.

According to still another aspect of the present invention, the present invention provides a method of improving skin wrinkles, which includes applying the peptide or the cosmetic composition onto the skin or the skin on which wrinkles appear.

According to yet another aspect of the present invention, the present invention provides a method of suppressing sebum production, which includes applying the peptide or the cosmetic composition onto the skin.

According to yet another aspect of the present invention, the present invention provides a method of ameliorating acne, which includes applying the peptide or the cosmetic composition onto the skin or the skin on which the acne appear.

According to the present invention, the application may include application onto the skin, but the present invention is not limited thereto.

The cosmetic composition is as described in the section "3: Cosmetic composition including peptide of the present invention."

An effective amount of the peptide including the amino acid sequence of SEQ ID NO: 1, or the cosmetic composition including the peptide may be applied/administered to a subject in need thereof.

Hereinafter, the present invention will be described in detail with reference to Preparation Examples, Examples, and Experimental Examples thereof.

However, it should be understood that the following Preparation Examples, Examples, and Experimental Examples are given for the purpose of illustration of the present invention only, and are not intended to limit the scope of the present invention.

Preparation Example 1: Preparation of Novel Peptide Having Various Physiological Activities A novel peptide sequence 'KFLIK' having an amino acid sequence set forth in SEQ ID NO: 1 was prepared using a known method. A molecular weight of the novel peptide was 647.4 Da.

Experimental Example 1: Evaluation of High-Temperature Stability of Peptide 1-1: Evaluation of High-Temperature Stability Upon Long-Term Storage The peptide of the present invention having the amino acid sequence of SEQ ID NO: 1 was dissolved at a concentration of 1,000 ppm in sterile distilled water, stored at 45° C. for 7 days, 14 days, 28 days, 60 days, and 75 days, and then subjected to a HPLC assay.

As a result, as shown in FIG. 1, it can be seen that the stability of the peptide of the present invention was maintained for the maximum observation time of 75 days under the condition of 45° C.

1-2: Evaluation of High-Temperature Stability

The peptide of the present invention was dissolved at a concentration of 1,000 ppm in sterile distilled water, warmed at 121° C. for 15 minutes and 30 minutes, and then subjected to a HPLC assay.

As a result, as shown in FIG. 2, it can be seen that the stability of the peptide of the present invention was maintained at 121° C. for the maximum warming time of 30 minutes.

Experimental Example 2: Confirmation of Decomposition Degree of Syntaxin 1A by Peptide A soluble N-ethylmaleimide sensitive factor attachment protein receptor (SNARE) protein participates in a membrane fusion occurring in the cells. The neuronal SNARE participating in the neurotransmission is associated with the binding of synaptic vesicles to a presynaptic membrane. The synaptic vesicles carrying neurotransmitters while releasing the neurotransmitters should be fused with the presynaptic membrane to form a neurotransmitter release channel. In this case, the fusion occurs by means of the SNARE present as a protein complex. In particular, a t-SNARE complex, which is a complex of a SNAP-25 protein and a syntaxin 1A protein attached to a target membrane, and v-SNARE attached to the vesicles are involved in the fusion. When the SNARE conjugation and twisting processes are not fully completed, the membrane fusion failed. Therefore, the muscles are relaxed because the neurotransmitters are not released. It was confirmed whether the peptide of the present invention had an ability to decompose syntaxin 1A constituting the t-SNARE.

2-1: Confirmation of Decomposition Degree of Recombinant Syntaxin 1A

In an experimental group, a reaction buffer solution (50 mM HEPES, 40 mM 2-ME, 20 μM $ZnCl_2$, pH 7.4) was treated with 1 μg of a recombinant syntaxin 1A protein (Novus biologicals, USA) and an increasing concentration (20 μM, 100 μM, and 200 μM) of the peptide of the present invention. In the negative control (Control), the reaction buffer solution was treated only with a recombinant syntaxin 1A protein. The resulting mixture was reacted for 4 hours under the condition of 37° C., and then subjected to Western blotting using a syntaxin 1A antibody (Synaptic Systems, Germany).

As a result, it was confirmed that, when the solution was treated with the peptide of the present invention, a band of the recombinant syntaxin 1A protein was reduced by the peptide of the present invention in a concentration-dependent manner, compared to the negative control in which the solution was not treated with the peptide of the present invention (FIG. 3).

2-2: Confirmation of Decomposition Degree of Endogenous Syntaxin 1A Expressed in Cells A reaction buffer solution (50 mM HEPES, 40 mM 2-ME, 20 μM $ZnCl_2$, pH 7.4) was treated with 30 μg of a SH-SY5Y cell lysate and an increasing concentration (20 μM, 100 μM, and 200 μM) of the peptide of the present invention. In the positive control (BoNT/C LC), a light chain (BoNT/C LC) of 0.2 μM *Botulinum* neurotoxin type C was used instead of the peptide of the present invention, and the sample was treated only with 30 μg of the SH-SY5Y cell lysate in the case of negative control (Control). Each of the mixtures was reacted at 37° C. for 4 hours. The reaction mixture was subjected to Western blotting using a syntaxin 1A antibody (Synaptic Systems, Germany).

As a result, it was confirmed that, when the solution was treated with the peptide of the present invention, a band of the recombinant syntaxin 1A protein was reduced by the peptide of the present invention in a concentration-dependent manner, like the positive control in which the solution was treated with BoNT/C LC (FIG. 4).

Summary of Experimental Example 2: The peptide of the present invention decomposes the recombinant syntaxin 1A or the endogenous syntaxin 1A, and thus the SNARE complex is not formed. Therefore, it is expected for the peptide of the present invention to have a muscle relaxation effect because the release of the neurotransmitters is not made.

Experimental Example 3: Analysis of Formation of SNARE Complex 3-1: Analysis Using Western Blotting It was confirmed whether a SNARE complex being formed in the cells was inhibited by an action of decomposition of syntaxin 1A by the peptide of the present invention. Specifically, after the Western blotting was performed, the density of a band of the SNARE complex having an expected size was determined. SH-SY5Y cells were seeded at a density of $3\times10^5$ cells/well in a 6-well plate. After the cells were cultured overnight, the medium was replaced with serum-free DMEM. The resulting culture solution was treated with an increasing concentration (10 μM, 50 μM, and 100 μM) of the peptide of the present invention. In the case of the positive control, the solution was treated with 0.2 μM BoNT/C LC. In the negative control (Control), the sample was not treated. After 24 hours of the sample treatment, the cells were collected, and a lysate was obtained, and then subjected to Western blotting using a syntaxin 1A antibody (Synaptic Systems, Germany). The band size of the SNARE complex was 75 kDa.

Based on the Western blotting results, it was observed that, when the solution was treated with the peptide of the present invention, the formation of the SNARE complex in the SH-SY5Y cells was inhibited, like the positive control in which the solution was treated with the BoNT/C LC (FIG. 5). Considering the results of Experimental Example 2, it was expected that the formation of the SNARE complex was inhibited due to an effect of the peptide of the present invention on the decomposition of syntaxin 1A.

3-2: Analysis Using Coimmunoprecipitation (Co-IP)

Coimmunoprecipitation was used for the purpose of detecting a protein that binds to another certain protein under non-denaturing conditions. SH-SY5Y cells were seeded at a density of $3\times10^5$ cells/well in a 6-well plate. When the cells were cultured overnight, the medium was replaced with serum-free DMEM. The resulting culture solution was treated with a 50 μM concentration of the peptide of the present invention for 24 hours. In the case of the positive control, the solution was treated with 0.2 μM BoNT/C LC. In the negative control (Control), the sample was not treated. A cell lysate was obtained, and subjected to immunoprecipitation using an SNAP-25 antibody (Synaptic Systems, Germany), followed by Western blotting using an SNAP-25 antibody and a syntaxin 1A antibody (Synaptic Systems, Germany).

As a result, it was confirmed that the interaction between the SNAP-25 and the syntaxin 1A was inhibited as the formation of the SNARE complex in the SH-SY5Y cells was suppressed by the treatment with the peptide of the present invention (FIG. 6). In FIG. 6, "IP input" represents an amount of the syntaxin 1A protein SNAP-25 found in the cell lysate obtained before the IP, and "Immunoprecipitation: anti-SNAP-25" represents the results obtained by treating the resulting product, which was obtained after the immunoprecipitation using the SNAP-25 antibody, with the SNAP-25 antibody or the syntaxin 1A antibody. That is, in the "Immunoprecipitation: anti-SNAP-25", a 'SNAP-25' panel shows the results obtained by re-detecting SNAP-5, which was precipitated by the SNAP-25 antibody in the cell lysate, and a 'syntaxin 1A' panel shows the results obtained by detecting the precipitate, which was precipitated by the SNAP-25 antibody in the cell lysate, using the syntaxin 1A antibody. It can be seen that the SNARE complex was not formed because an amount of the syntaxin 1A was maintained in the negative control (Control) in which the sample was not treated in the 'syntaxin 1A' panel. Also, it can be seen that the formation of the SNARE complex was inhibited because an amount of the syntaxin 1A was reduced in the inventive peptide-treated group and the BoNT/C LC-treated group.

Summary of Experimental Example 3:

It can be seen that the formation of the SNARE complex was inhibited during treatment with the peptide of the present invention. Considering the results of Experimental Example 2, it can also be seen that the syntaxin 1A was decomposed by the treatment with the peptide of the present invention, thereby inhibiting the formation of the SNARE complex. Therefore, it was expected that the peptide of the present invention had a muscle relaxation effect because the neurotransmitters were not released as the formation of the SNARE complex was inhibited.

Experimental Example 4: Confirmation of Inhibitory Effect of Peptide on Acetylcholine Secretion It was verified whether the peptide of the present invention including the amino acid sequence of SEQ ID NO: 1 had an inhibitory effect on acetylcholine secretion. Human bone marrow neuroblastoma SH-SY5Y cells were seeded, and cultured for 24 hours in a $CO_2$ incubator. The medium was replaced with a serum-free medium, and the cells were cultured for 48 hours. The resulting culture solution was treated with an increasing concentration (1 µM, 10 µM, and 50 µM) of the peptide of the present invention, and then treated with 50 nM tetanus as the positive control. Also, the culture solution was treated with nicotine (NIC) plus potassium chloride (KCl) as an inducing factor for promoting the acetylcholine secretion, and then cultured for 30 minutes. A group in which the culture solution was treated with nicotine and potassium chloride but not treated with the peptide of the present invention or the tetanus was used as the negative control. When the culturing was completed, the medium was separated, and a secretion level of acetylcholine included in the medium was measured using a choline/acetylcholine analysis kit.

As shown in FIG. 7, it was confirmed that the peptide of the present invention reduced the content of acetylcholine in a concentration-dependent manner with respect to the level of acetylcholine secreted in the normal group (Control). Also, it was confirmed that the peptide of the present invention has an excellent inhibitory effect on the acetylcholine secretion when the sample was treated with a 50 µM concentration of the peptide of the present invention, compared to the positive control in which the sample was treated with tetanus.

Experimental Example 5: Confirmation of Effect on Relaxation of Mouse Toe Muscle 100 µg of the peptide of the present invention was administered to the calf muscle from C57BL/6 female 7-week-old mice, and then observed. A muscle relaxation effect was determined using a digit abduction scoring (DAS) assay. The abduction refers to a motion of stretching out the limbs, and the DAS is obtained by measuring a degree of decrease in ability of an animal triggering a startle response in the calf muscle. The DASs are divided into scores 0 to 4. In this case, the higher score means the higher muscle relaxation effect (FIG. 8A). That is, the higher score means that the startle response is more inhibited by means of mechanisms such as acetylcholine secretion suppression, and the like. Score 0 represents that all five toes are separated, Score 1 represents that two mouse toes are fixed during the abduction, Score 2 represents that a big toe and two toes are not separated, Score 3 represents that a big toe and three toes were fixed, and Score 4 represents that all five toes are fixed.

As shown in FIG. 8b, the startle response occurred before the treatment with the peptide of the present invention, all the five toes were separated, which was given Score 0. On the other hand, the muscle relaxation action of the peptide of the present invention increases the DAS scores after 3 hours of injection of the peptide of the present invention, and Score 4 was recorded after 17 hours of injection of the peptide of the present invention Experimental Example 6: Comparison Between Muscle Relaxation Effects of Peptide and Botox 100 µg of the peptide of the present invention and 0.6 units of BTX-A type (BoNT-A) were injected to each of the calf muscles from two C57BL/6 female 7-week-old mice, and then subjected to a DAS assay.

As shown in FIGS. 9 and 10, the inventive peptide-administered group showed a superior muscle relaxation effect after 20 hour of administration, compared to the non-administered group, and had an effect similar to the BoNT-A.

Summary of Experimental Examples 4 to 6:

The peptide of the present invention may be effectively used to ameliorate a neuromuscular disease or improve wrinkles because the peptide of the present invention suppresses the acetylcholine secretion in vitro, and shows an in vivo muscle relaxation effect similar to the Botox.

Experimental Example 7: Confirmation of Penetration of Peptide into Cells or Tissue Penetration Pattern A 'rhodamine-inventive peptide' conjugate used to confirm penetration of the peptide of the present invention into cells or a tissue penetration pattern was prepared, as follows. 10 mg/mL of the peptide of the present invention solution was prepared using 100 mM sodium bicarbonate (pH 9.0). 1 mg/mL of an NHS-rhodamine (Thermo Scientific, 46406) solution was prepared using dimethyl formamide. The solutions were mixed so that a molar ratio of the peptide of the present invention and the NHS-rhodamine conjugate was 1:10. After shielding the light, the resulting mixture was reacted at room temperature for an hour while inverting. The reaction solution was dialyzed, and then subjected to LC/MS to confirm the conjugation between rhodamine and the peptide of the present invention.

7-1: Confirmation of Penetration of Peptide into Cells

SH-SY5Y cells were seeded at a density of $3 \times 10^5$ cells/well in a 6-well plate. After the cells were cultured overnight, the medium was replaced with a serum-free DMEM. The culture solution was treated with an increasing concentration of the peptide of the present invention labeled with a fluorescent material (i.e., rhodamine) for 4 hours. After 4 hours, the culture solution was treated with 4% paraformaldehyde to fix the cells. Thereafter, the cells were subjected to nuclear staining using a DAPI staining kit (Invitrogen, USA). The penetration of the peptide into the cells was observed using a fluorescence microscope. Blue represents the nuclei of the cells stained with DAPI, and red represents a 'rhodamine-inventive peptide' conjugate.

As shown in FIG. 11, it was confirmed that the peptide of the present invention penetrated into the SH-SY5Y cells when the culture solution was treated with the peptide of the present invention.

7-2: Confirmation of Tissue Penetration Pattern of Peptide

Hair was removed from the back of a 7-week-old SD rat, and rhodamine and the peptide of the present invention were applied onto the rat's back. After an hour, the rat was sacrificed for analysis. An applied part of the skin tissue was collected, and fixed in formalin for a day. A paraffin block was prepared from the fixed tissue, and microtomed into slices, which were than subjected to immunohistochemical staining using a neuronal marker TrkB Ab (Cell Signaling, USA). Thereafter, the cells were subjected to nuclear staining using a DAPI staining kit (Invitrogen, USA). The penetration of the peptide into the cells was observed using a fluorescence microscope. Blue represents the nuclei of the cells stained with DAPI, red represents a 'rhodamine-inventive peptide' conjugate, and green represents TrkB (a nerve fiber marker).

From the obtained results, it was confirmed that the peptide of the present invention penetrated to the tunica muscularis of the skin tissue when the skin was treated with the peptide of the present invention, as shown in FIG. 12. Also, it was confirmed that the peptide of the present invention was co-localized with the neuronal marker. When the enlarged image of FIG. 12 was observed, it was confirmed that the peptide of the present invention and the neurons around the hair follicles or sebaceous glands were co-localized (FIGS. 13 and 14).

Summary of Experimental Example 7:

The peptide of the present invention may penetrate into the cells, penetrates to the tunica muscularis of the skin tissue, and is co-localized with the neuronal marker in the tunica muscularis. Therefore, it is expected that the peptide of the present invention participates in formation of the SNARE complex participating in delivery of neurotransmitters of the neurons, thereby showing a muscle relaxation effect.

Experimental Example 8: Confirmation of Wrinkle Improvement Effect of Peptide (Increased Expression of Dermal Components A liposome solution including 4,000 ppm of the peptide of the present invention was applied onto the back of a 7-week-old hair-less mouse twice a day for a total of 12 weeks. After the applied part was observed with the naked eye, the skin tissue was collected, and fixed in formalin. A paraffin block was prepared from the fixed tissue, and microtomed to prepare tissue slides.

8-1: Confirmation of Wrinkle-Reducing Effect

In the group of mice on which a liposome solution including the peptide of the present invention was applied for 12 weeks, the mice were observed with the naked eye and observed under a microscope. As a result, it was observed that the wrinkles were significantly reduced with the muscle relaxation effect in all the mice, compared to the control on which only the liposome solution was applied (FIGS. 15 and 16).

8-2: Evaluation of Expression Level of Collagen

The tissue slides were stained using a Masson's Trichrome staining kit (Abcam, USA), and then observed using an optical microscope.

It was confirmed that an expression level of collagen increased in the group of mice on which the liposome solution including the peptide of the present invention was applied for 12 weeks, compared to the control on which only the liposome solution was applied (FIG. 17).

8-3: Evaluation of Expression Levels of Elastin and Fibronectin

The tissue slides were subjected to immunohistochemical staining using an elastin antibody and a fibronectin antibody (Cell signaling, USA), followed by nuclear staining using a DAPI staining kit (Invitrogen, USA). The stained tissue slides were observed using a fluorescence microscope.

It was confirmed that expression levels of elastin and fibronectin increased in the group of mice on which the liposome solution including the peptide of the present invention was applied for 12 weeks, compared to the control on which only the liposome solution was applied (FIGS. 18 and 19).

Experimental Example 9: Confirmation of Inhibitory Effect of Peptide on Sebum Production A liposome solution including 4,000 ppm of the peptide of the present invention was applied onto the back of a 7-week-old hair-less mouse twice a day for a total of 12 weeks. After the applied part was observed with the naked eye, the skin tissue was collected, and fixed in formalin. A paraffin block was prepared from the fixed tissue, and microtomed to prepare tissue slides. The tissue slides were subjected to immunohistochemical staining using a fatty acid synthase antibody (Cell Signaling, USA) as the sebum production-related marker, and the stained tissue slides were observed using an optical microscope.

It was confirmed that the number of sebaceous glands was reduced, and an expression level of the sebum production-related marker was lowered in the group of mice on which the liposome solution including the peptide of the present invention was applied for 12 weeks, compared to the control on which only the liposome solution was applied (FIG. 20). The left panel of FIG. 20 shows the results obtained by applying the liposome which did not include the peptide for 12 weeks, and the right panel shows the results obtained by applying the liposome including 4,000 ppm of the peptide for 12 weeks. In this regard, it can be seen that the brown-looking immunostained parts were faded in color and the number of the immunostained parts was reduced as the peptide liposome was applied.

Preparation Example 2: Preparation of Cosmetic Formulation 2-1: Preparation of Essence An essence was prepared using the peptide of the present invention, based on the contents (part(s) by weight) listed in the following Table 1.

TABLE 1

| Compositions | Contents (part(s) by weight) |
| --- | --- |
| Triethanolamine | 0.25 |
| Carboxyvinyl polymer | 0.22 |
| Glycerin | 4 |
| Butylene glycol | 2 |
| Inventive peptide | 1.5 |
| Beeswax | 0.5 |
| Cetostearyl alcohol | 1 |
| Glyceryl monostearate | 1 |
| Squalene | 4 |
| Purified water | Proper amount |

2-2: Preparation of Toner

A toner including the peptide of the present invention as the active ingredient was prepared as listed in the following Table 2.

TABLE 2

| Base materials | Contents (part(s) by weight) |
| --- | --- |
| 1,3-butylene glycol | 1.00 |
| Disodium EDTA | 0.05 |
| Allantoin | 0.10 |
| Dipotassium glycyrrhizate | 0.05 |
| Citric acid | 0.01 |
| Sodium citrate | 0.02 |

TABLE 2-continued

| Base materials | Contents (part(s) by weight) |
|---|---|
| Glycereth-26 | 1.00 |
| Arbutin | 2.00 |
| PEG-40 hydrogenated castor oil | 1.00 |
| Ethanol | 30.00 |
| Inventive peptide | 1.5 |
| Coloring agent | Trace |
| Flavoring agent | Trace |
| Purified water | Balance |

2-3: Preparation of Nourishing Cream

A nourishing cream including the peptide of the present invention as the active ingredient was prepared based on the compositions as listed in the following Table 3.

TABLE 3

| Base material | Contents (part(s) by weight) |
|---|---|
| 1,3-Butylene glycol | 7.0 |
| Glycerin | 1.0 |
| D-Panthenol | 0.1 |
| Magnesium aluminum silicate | 0.3 |
| PEG-40 stearate | 1.2 |
| Stearic acid | 2.0 |
| Polysorbate 60 | 1.5 |
| Glyceryl stearate, lipophilic | 2.0 |
| Sorbitan sesquioleate | 1.5 |
| Cetearyl alcohol | 3.0 |
| Mineral oil | 4.0 |
| Squalene | 3.8 |
| Inventive peptide | 1.5 |
| Vegetable oil | 1.8 |
| Dimethicone | 0.4 |
| Dipotassium glycyrrhizate | Trace |
| Allantoin | Trace |
| Sodium hyaluronate | Trace |
| Tocopheryl acetate | Proper amount |
| Triethanolamine | Proper amount |
| Flavoring agent | Proper amount |
| Purified water | Balance |

2-4: Preparation of Lotion

A lotion including the peptide of the present invention as the active ingredient was prepared based on the compositions as listed in the following Table 4.

TABLE 4

| Base material | Contents (part(s) by weight) |
|---|---|
| Cetostearyl alcohol | 1.6 |
| Stearic acid | 1.4 |
| Monostearic acid glycerin, lipophilic | 1.8 |
| PEG-100 stearate | 2.6 |
| Sorbitan sesquioleate | 0.6 |
| Squalene | 4.8 |
| Macadamia oil | 2 |
| Jojoba oil | 2 |
| Tocopherol acetate | 0.4 |
| Methtyl polysiloxane | 0.2 |
| Tocopherol acetate | 0.4 |
| 1,3-Butylene glycol | 4 |
| Xanthan gum | 0.1 |
| Glycerin | 4 |
| D-Panthenol | 0.15 |
| Inventive peptide | 1.0 |
| Allantoin | 0.1 |
| Carbomer (2% aq. Sol) | 4 |
| Triethanolamine | 0.15 |
| Ethanol | 3 |
| Purified water | Proper amount |

Preparation Example 3: Preparation of Pharmaceutical Composition 3-1: Preparation of Powder

| | |
|---|---|
| Inventive peptide | 2 g |
| Lactose | 1 g |

The components were mixed, and then filled in an airtight pack to prepare a powder.

3-2: Preparation of Tablet

| | |
|---|---|
| Inventive peptide | 100 mg |
| Corn starch | 100 mg |
| Lactose | 100 mg |
| Magnesium stearate | 2 mg |

The components were mixed, and then tablet-pressed to prepare a tablet according to a conventional method of preparing a tablet.

3-3: Preparation of Capsule

| | |
|---|---|
| Inventive peptide | 100 mg |
| Corn starch | 100 mg |
| Lactose | 100 mg |
| Magnesium stearate | 2 mg |

The components were mixed, and then filled in a gelatin capsule to prepare a capsule according to a conventional method of preparing a capsule.

3-4: Preparation of Pill

| | |
|---|---|
| Inventive peptide | 1 g |
| Lactose | 1.5 g |
| Glycerin | 1 g |
| Xylitol | 0.5 g |

The components were mixed, and then processed according to a conventional method to prepare a pill so that the components were included at a content of a total of 4 g per pill.

3-5: Preparation of Granule

| | |
|---|---|
| Inventive peptide | 150 mg |
| Soybean extract | 50 mg |
| Glucose | 200 mg |
| Starch | 600 mg |

The components were mixed, and 100 mg of 30% ethanol was then added thereto. The resulting mixture was dried at a Celsius degree of 60° C. to form a granule, which was then filled in a pack.

The invention claimed is:

1. A method for relaxing muscles in a subject in need thereof, the method comprising administering to the subject a pharmaceutical composition, wherein the pharmaceutical composition comprises an effective amount of a peptide comprising the amino acid sequence set forth in SEQ ID NO: 1.

2. The method of claim 1, wherein the peptide is included at a content of 0.001% by weight to 60% by weight, based on 100% by weight of the pharmaceutical composition.

3. A method for treating a neuromuscular disease in a subject in need thereof, the method comprising administering to the subject a pharmaceutical composition, wherein the pharmaceutical composition comprises an effective amount of a peptide comprising the amino acid sequence set forth in SEQ ID NO: 1.

4. The method of claim 3, wherein the neuromuscular disease comprises any one selected from the group consisting of eyelid twitching, torticollis, cervical dystonia, tonic blepharospasm, axillary hyperhidrosis, anal fissure, colpospasm, achalasia, a headache disorder, idiopathic and neurogenic detrusor overactivity, focal dystonia, temporomandibular joint pain/disorder, diabetic neuropathy, vocal cord dysfunction, strabismus, chronic neuropathy, facial muscular hypertrophy, detrusor-sphincter dyssynergia, and benign prostatic hyperplasia.

5. The method of claim 4, wherein the headache disorder is migraine.

6. The method of claim 3, wherein the peptide suppresses secretion of acetylcholine.

7. A method for improving a skin condition in a subject in need thereof, the method comprising administering to the subject a cosmetic composition, wherein the cosmetic composition comprises an effective amount of a peptide comprising the amino acid sequence set forth in SEQ ID NO: 1.

8. The method of claim 7, wherein the skin condition comprises skin wrinkles, sebum production, acne, or combinations thereof.

9. The method of claim 7, wherein the peptide is included at a content of 0.001% by weight to 60% by weight, based on 100% by weight of the cosmetic composition.

10. The method of claim 7, wherein the peptide increases expression of collagen.

11. The method of claim 1, wherein the peptide suppresses secretion of acetylcholine.

* * * * *